US010603267B2

(12) United States Patent
Streuli

(10) Patent No.: US 10,603,267 B2
(45) Date of Patent: Mar. 31, 2020

(54) DURABLE STYLING COMPOSITIONS AND THE USES THEREOF

(71) Applicant: ISP INVESTMENTS INC., Wilmington, DE (US)

(72) Inventor: David C. Streuli, Wayne, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 23 days.

(21) Appl. No.: 15/053,843

(22) Filed: Feb. 25, 2016

(65) Prior Publication Data

US 2016/0235649 A1    Aug. 18, 2016

Related U.S. Application Data

(62) Division of application No. 13/990,966, filed as application No. PCT/US2011/062874 on Dec. 1, 2011, now abandoned.
(Continued)

(51) Int. Cl.
*A61K 8/81* (2006.01)
*A61Q 5/06* (2006.01)
(Continued)

(52) U.S. Cl.
CPC .............. *A61K 8/8182* (2013.01); *A45D 7/06* (2013.01); *A61K 8/342* (2013.01); *A61K 8/41* (2013.01);
(Continued)

(58) Field of Classification Search
None
See application file for complete search history.

(56) References Cited

U.S. PATENT DOCUMENTS 5,254,333 A * 10/1993 Kajino ................... A61K 8/817
424/70.11
6,093,410 A * 7/2000 Peffly ..................... A61K 8/068
424/401

(Continued)

FOREIGN PATENT DOCUMENTS

WO    WO2010020501 A2    2/2010

OTHER PUBLICATIONS

International Search Report, PCT/US2011/062874, published on Jun. 7, 2012.

*Primary Examiner* — Carlos A Azpuru
*Assistant Examiner* — Casey S Hagopian
(74) *Attorney, Agent, or Firm* — William J. Davis; Nathalie Tietcheu

(57) ABSTRACT

Compositions are disclosed that impart one or more durable hair styling benefits. The durable styling compositions comprise at least a first compound having anhydride, diacid, diester, or half-acid/half-ester functionality, and a second compound having at least one amine moiety or hydroxyl functional group. In one embodiment the durable styling composition takes the form of a leave-in product. The durable styling compositions are heat-activated, which may be accomplished through the use of a heated styling tool like a flat-iron, curling iron, and/or hair dryer. The benefits include shine, conditioning, softness, defrizzing, and improved hair alignment, and endure for up to 5 wash cycles or more without having to reapply the durable styling composition nor heat.

17 Claims, 26 Drawing Sheets

Related U.S. Application Data

(60) Provisional application No. 61/418,539, filed on Dec. 1, 2010.

(51) Int. Cl.
*A61K 8/41* (2006.01)
*A61K 8/73* (2006.01)
*A61K 8/34* (2006.01)
*A45D 7/06* (2006.01)
*A61Q 5/12* (2006.01)

(52) U.S. Cl.
CPC ............ *A61K 8/731* (2013.01); *A61K 8/8152* (2013.01); *A61K 8/8164* (2013.01); *A61Q 5/06* (2013.01); *A61Q 5/12* (2013.01); *A61K 2800/594* (2013.01)

(56) References Cited

U.S. PATENT DOCUMENTS

| | | | |
|---|---|---|---|
| 6,241,977 B1 * | 6/2001 | McMullen, Jr. | A61K 8/8164 132/202 |
| 6,395,258 B1 | 5/2002 | Steer | |
| 7,402,301 B2 * | 7/2008 | Candau | A61K 8/19 424/400 |
| 2003/0008855 A1 * | 1/2003 | Simon | A61K 8/23 514/184 |
| 2008/0299154 A1 | 12/2008 | Barrios et al. | |
| 2010/0021410 A1 * | 1/2010 | Glynn, Jr. | A61K 8/34 424/70.21 |
| 2010/0047202 A1 | 2/2010 | Goddinger et al. | |
| 2011/0165109 A1 | 7/2011 | Müller et al. | |
| 2011/0293540 A1 | 12/2011 | Musa et al. | |

* cited by examiner

DURABLE STYLING COMPOSITIONS AND THE USES THEREOF

CROSS-REFERENCE TO RELATED APPLICATIONS

This application is a divisional of U.S. application Ser. No. 13/990,966 filed Dec. 1, 2011 which was the National Stage of International Application No. PCT/US2011/062874, filed Aug. 6, 2013 which claims the benefit of U.S. Provisional Application No. 61/418,539 filed Dec. 1, 2010. The entire contents of the related applications set forth herein are hereby incorporated by reference.

FIELD OF THE INVENTION

The invention relates to compositions for hair care, and more specifically, to compositions that impart a durable hair styles that last for up to 5 wash cycles or more.

BACKGROUND OF THE INVENTION

Many people express interest in hair styling benefits like shine, softness, and manageability, especially for wavy, curly, or frizzy hair. Typically, these benefits are attained using hair care products like rinse-off shampoos and conditioners, and leave-in products that are not washed off like gels and mousses. Likewise, people with straight hair often curl their hair to change their hair style and appearance. Curling irons and hair curlers can provide curls and/or waves, which are then held in place using hair spray. In both scenarios, however, the results are often short-lived as the hair styling benefits are not durable, but rather are lost after washing. Other styling products, like permanent wave and high-pH hair straightening formulas, achieve a permanent hair style by altering the chemical nature of the internal hair structure. Due to the chemical processes involved, these "permanent" products may achieve long-enduring style at the cost of considerable damage to the hair. Additionally, consumers may find the results last too long, and therefore do not enjoy the option of being able to undo the style without cutting off the hair or risking further chemical modification of the hair.

Hence, there is a need for hair styling products that provide durable, but not permanent benefits without being harsh or damaging to hair.

SUMMARY OF THE INVENTION

The invention provides compositions and methods for delivering durable hair styling benefits. These compositions comprise a first compound having diacid, diester, half-acid/half-ester, or anhydride functionality, and a second compound having at least one amine moiety or hydroxyl functional group. The first and second compounds may be different compounds or the same compound having both functionalities. In a first embodiment the first compound is one or more polymers having diacid functionality, like maleic acid groups (like PVM/MA copolymer) or their ethyl, isopropyl, and butyl half-ester counterparts. Combinations of these polymers may be used. The second compound also may be a polymer, such as polyimide-1. Other examples of the first and second compounds are provided herein. These durable styling compositions may take the form of leave-in hair care products, like sprays, lotions, mists, and mousses, and may be applied to damp hair, for example, after shampooing.

After application to hair, heat from a hair dryer, flat-iron, curling iron, or similar tool activates the composition to create durable styling benefits that persist for up to five wash cycles or more, without the need to reapply the invention's composition nor heat. These durable styling benefits include, but are not limited to, softness, defrizzing, decurling and/or dewaving (or curls and/or waves when imparting these styles to straight hair), shine enhancement, improved hair alignment, and better manageability.

DETAILED DESCRIPTION

Figure 1A:
FIG. 1A-1D are photographs of hair treated in accordance with Example 289.

Described herein are compositions that impart one or more durable styling benefits to hair, and to the methods to attain these benefits. The inventors have found improvement in softness, defrizzing, decurling, dewaving, shine, hair alignment, and management that last for up to 5 wash cycles or more after treatment without the need to reapply the durable style composition nor the activating heat treatment. Without being bound by theory, it is believed these compositions provide a surface treatment with hair, and in this way are not harsh nor damaging to hear like permanent wave or high-pH straightening preparations.

All percentages, ratio, and proportions used herein are based on a weight basis unless otherwise specified.

Description of the Compositions

The durable styling compositions prescribed herein comprise at least one first compound having acid functionality. In various embodiments, this first acid-compound is a polymer, oligomer, or small molecule having diacid, diester, or half-ester/half-acid functionality, e.g., at least one repeating unit based on a structure represented by:

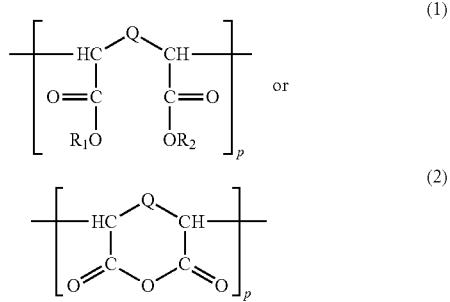

wherein Q is selected from the group consisting of a direct bond and alkylene, $R_1$ and $R_2$ are independently selected from the group consisting of: hydrogen, alkyl groups, alkali metals, and alkaline earth metals; and p is an integer greater than 2. In one embodiment, the alkyl group is methyl, ethyl, propyl, isopropyl, or butyl. In theory, any alkyl group can be employed for $R_1$ and/or $R_2$ of structure (1), as it is a leaving group during heat-induced dehydration to form the corresponding anhydride analogue. Suitable alkali and alkaline earth metals include sodium, calcium, and potassium. Various combinations of $R_1$ and/or $R_2$ can be used.

In another embodiment of the invention, Q is a direct bond, so that the repeating units shown in (1) and (2) can be represented by the structures:

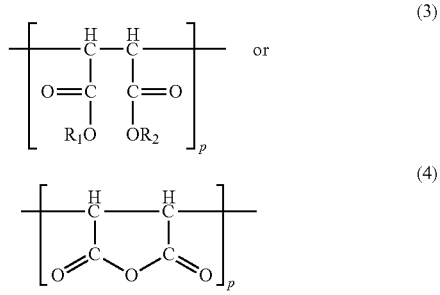

wherein $R_1$, $R_2$, and p retain their earlier definitions.

It will be recognized by one skilled in the art that the structures represented in (1) and (3) dehydrate when heated to form the anhydrides represented by structures (2) and (4). As described in U.S. Pat. No. 6,241,977, which is incorporated herein its entirety by reference, the anhydride moiety is believed to be reactive to amino acids in hair, first forming a maleamic acid that dehydrates when heated to yield a succinimide functionalized analogue that covalently bonds this first compound of the invention to hair.

As may be the case, the first compound having at least one repeating unit represented by structures (1) and/or (2) also will have other repeating units, i.e., the first compound may be a polymer that is a non-homopolymer. These other repeating units and the amounts of each unit can be selected to modulate the polymer's properties, especially with respect to molecular weight, water solubility, film-formation, glass transition temperature, viscosity, and benefits imparted to hair. For example, such a non-homopolymer may also have at least one other unit selected from: adipic acid benzoic acid butyl benzoic acid decadiene, ethylene, isobutene, isooctylene, (meth)acrylic esters of saturated or unsaturated cyclic or bicyclic alcohols having 6 to 20 carbon atoms, (meth)acrylic esters of a straight- or branched-chain alkyl alcohols, neopentyl glycol octadecene palmitic acid pentaerythritol/neopentyl glycol phthlatic anhydride styrene, trimethylolethane vinyl acetate, or vinyl alkyl ethers. As the Examples illustrate, combinations of these other repeating units find usefulness.

Some examples of these non-homopolymers suitable as the first compound are: adipic acid/neopentyl glycol/trimellitic anhydride copolymer, benzoic acid/phthalic anhydride/pentaerythritol/neopentyl glycol/palmitic acid copolymer, butyl benzoic acid/phthalic anhydride/trimethylolethane copolymer, butyl ester of ethylene/MA copolymer, butyl ester of PVM/MA copolymer, calcium/sodium salt of PVM/MA copolymer, ethyl ester of PVM/MA copolymer, ethylene/MA copolymer, isobutylene/MA copolymer, isopropyl ester of PVM/MA copolymer, octadecene/MA copolymer, phthalic anhydride/adipic acid/castor oil/neopentyl glycol/PEG-3/trimethylolpropane copolymer, phthalic anhydride/benzoic acid/trimethylolpropane copolymer, phthalic anhydride/butyl benzoic acid/propylene glycol copolymer, phthalic anhydride/glycerin/glycidyl decanoate copolymer, phthalic anhydride/trimellitic anhydride/glycol copolymer, polyethylene/isopropyl maleate/MA copolymer, polyvinyl methyl ether (PVM)/MA copolymer, PVM/MA decadiene crosspolymer, sodium C4-C12 olein/maleic acid copolymer, sodium isooctylene/MA copolymer, sodium MA/diisobutylene copolymer, sodium PVM/MA/decadiene crosspolymer, stearylvinyl ether/MA copolymer, styrene/MA copolymer, and trimethylpentanediol/isophthalic acid/trimellitic anhydride copolymer. Note is made that the term "(meth)acrylic" is understood to represent both acrylic and methacrylic variants.

In one embodiment, the non-homopolymer comprises one or more repeating units based on alkyl vinyl ethers, such as C1-C20 vinyl ethers, including methyl vinyl ether, ethyl vinyl ether, octyl vinyl ether, dodecyl vinyl ether, lauryl vinyl ether, and eicosyl vinyl ether. These polymers also may comprise poly(vinyl methyl ether/maleic acid), its diester, half-acid/half-ester, and anhydride analogues, which are well known to the personal care arts. The invention also contemplates the use of mixed alkyl vinyl ether/maleic anhydride polymers, as well as their diacid and ester analogues. Disclosure of these polymers is provided in the following U.S. Pat. Nos. 3,625,924; 3,974,128; and 4,952,558. Also contemplated are the branched and crosslinked polymers described in U.S. Pat. No. 5,202,112 and application U.S. Provisional Application No. 61/565,656, filed on Dec. 1, 2011, entitled "Soluble Branched Polymers."

Also included are the (meth)acrylic esters of a straight- or branched-chain alkyl alcohols. Polymers with many different attributes can be created by selecting the straight- or branched-chain alkyl alcohols, for example, higher molecular weight alkyl alcohols are generally more hydrophobic than lower molecular weight alcohols having one to four carbon atoms. One (meth)acrylic ester of a straight-chain alkyl alcohol illustrated in the Examples is lauryl (meth)acrylate, which includes both lauryl methacrylate and lauryl acrylate.

(Meth)acrylic esters of saturated or unsaturated cyclic or bicyclic alcohols having 6 to 20 carbon atoms also may be selected as a comonomer to the repeating unit(s) represented in structures (1) or (2). A member of these (meth)acrylic esters is isobornyl (meth)acrylate.

Other examples of these comonomers that may be used to produce suitable first compounds of the invention are provided in the Examples.

Compounds comprising one or more structures represented by (2) and/or (4) may be functionalized, given the reactivity of the anhydride moiety. In this way additional functionality may be imparted to the first compound (A), especially those useful in the personal care and hair care arts. The term "functionalized" when used in regard to functionalized maleic (or itaconic) anhydride refers to reaction products wherein the anhydride moiety has been altered by a reaction such as, but not limited to: acylation, alkylation, amidation, cycloaddition, decomposition/decarboxylation, Diels-Alder reaction, electrophilic addition and nucleophilic addition, ene reaction, esterification, formation of acid chloride, Grignard reactions, halogenation, heterogeneous catalytic reduction, hydration and dehydration, hydroformylation, isomerization, ligation, Michael addition, and/or ozonolysis and oxidation. Such derivatization may involve some or all or the anhydride units of a first compound (A).

A few examples of functionalized anhydrides include those materials disclosed in WO 2001/002278, the contents of which are incorporated in their entirety by reference.

Also known is maleated soybean oil.

Many compounds possess maleic anhydride, diacid, diester, or half-acid/half-ester functionality, or a salt thereof, suggesting their suitability as a first compound to the invention's compositions. Table 1 summarizes a few of the possible choices, giving their international nomenclature of cosmetic ingredients (INCI) names and chemical structures. It will be appreciated that the crosslinked polymers such as PVM/MA decadiene crosslinked polymer have a more complicated structure than illustrated in Table 1, wherein crosslinking chains (e.g., decadiene) connect one or more polymer chains.

TABLE 1

A few polymers having anhydride/acid functionality

| INCI name | structure |
| --- | --- |
| polyimide-1 | [structure diagram] |
| PVM/MA decadiene crosspolymer | [structure diagram] (crosslinked with decadiene) |
| PVM/MA copolymer | [structure diagram] or [structure diagram] |
| ethyl ester of PVM/MA copolymer | [structure diagram] |

TABLE 1-continued

A few polymers having anhydride/acid functionality

| INCI name | structure |
|---|---|
| butyl ester of PVM/MA copolymer | [structure showing polymer with OCH₃, OH, and O(CH₂)₃CH₃ groups, subscript p] |
| isopropyl ester of PVM/MA copolymer | [structure showing polymer with OCH₃, OH, and OCH(CH₃)₂ groups, subscript p] |
| styrene/maleic diacid copolymer | [structure showing polymer with phenyl group and two OH groups, subscript p] |
| VA/butyl maleate/ isobornyl acrylate copolymer | [structure showing copolymer with OC(=O)CH₃, OH, OC₄H₉ groups, subscript m, and isobornyl acrylate group, subscript n] |

In another aspect of the invention, this first compound belongs to the poly(vinylmethyl ether-co-maleic anhydride) (PVM/MA) family of polymers, which includes the alkyl half-ester variants like ethyl ester, isopropyl ester, and butyl ester. It is recognized in the art the alkyl half-ester variants dehydrate at a lower temperature than maleic acid. This lower dehydration temperature may be beneficially exploited to decrease the first-time heat styling temperature.

Polyimide-1 and polymers like it find special use in the invention, and will described in more detail after discussing the second compound of the invention's compositions.

While the maleic anhydride moiety is believed to be reactive toward the amino acid groups of hair, maleic anhydride is relatively poorly water-soluble, but readily hydrolyzes in water or esterifies in the presence of alcohol(s), both of which enhance water solubility. Various salts of these acids can be created by pH adjustment using one or more acids or bases, such as sodium hydroxide, ammonium hydroxide, potassium hydroxide, and/or calcium hydroxide. Thus, while the invention prescribes a first compound of the durable styling composition having acid functionality, like maleic acid, a half acid, or a salt thereof, the invention also embraces maleic anhydride as this compound.

Also suitable as a first compound are those materials comprising trimellitic anhydride, its half-ester, its diacid, or combinations thereof. Trimellitic anhydride is recognized as having three maleic anhydride moieties. Representative materials include adipic acid/neopentyl glycol/trimellitic anhydride copolymer (CAS number 28407-73-0), and trimethylpentane-diol/isophthalic acid/trimellitic anhydride copolymer.

Referring back to structures (1) and (2), Q also describes repeating units based on itaconic acid, or a half-ester, diacid, or salt thereof. Representative materials based on itaconic anhydride include PVP/VA/itaconic acid copolymer (CAS number 68928-72-3).

In addition to this first compound, the durable styling composition also comprises at least one second compound having at least one amine moiety or hydroxyl functional group. Without being bound to theory, it is believed that these groups provides additional reactivity to the maleic anhydride moiety of the first compound, forming a covalently bonded, hydrogen bonded, and/or weakly associated matrix with hair. In another framework, quaternized nitrogen moieties are known to be substantive to hair, which also might provide the mechanism for the interaction. This second compound may be the same as or different from the abovedescribed first compound, as will be shown later.

In one embodiment, the second compound comprises a polymer. Suitable polymers include those approved for personal care compositions, and include polyimide-1, vinyl caprolactam/VP/dimethylaminoethyl methacrylate copolymer (and) lauryl pyrrolidone copolymer, polyquaternium-69, VP/vinyl caprolactam/DMAPA acrylate copolymer, VP/dimethylaminoethyl methacrylate copolymer, vinyl caprolactam/VP/dimethylaminoethyl methacrylate copolymer, quaternized copolymer of VP and dimethylaminoethyl methacrylate, copolymer of VP and methacrylamidopropyl trimethylammonium chloride, VP/dimethylaminopropyl methacrylamide copolymer, polyquaternium-55, polyquaternium-28, polyquaternium-7, and polyimide-1 functionalized to contain high amine content. The INCI name, trade name, and chemical structures of some of these polymers are provided in Table 2.

TABLE 2

Polymers having at least one amine moiety.

| INCI name | structure |
|---|---|
| vinyl caprolactam/ VP/dimethyl-aminoethyl methacrylate copolymer (and) lauryl pyrrolidone | 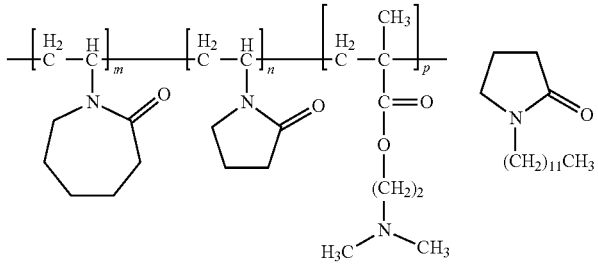 |
| polyquaternium-69 | 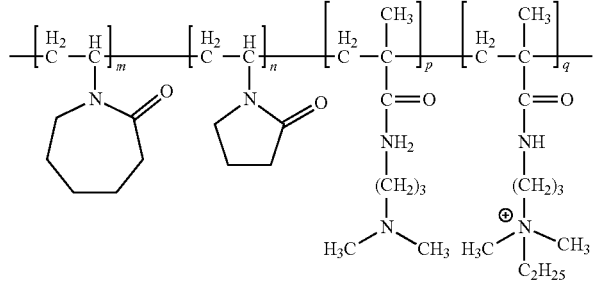 |
| VP/vinyl caprolactam/ DMAPMA acrylate copolymer | 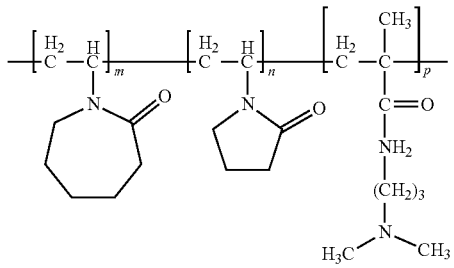 |
| polyimide-1 | 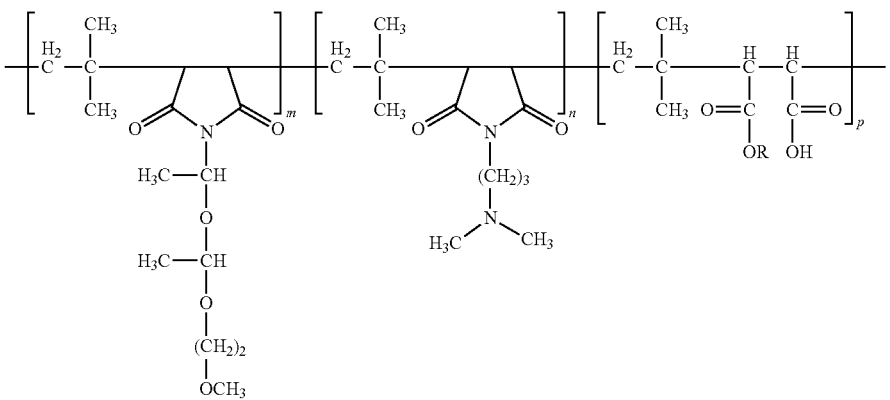 |

TABLE 2-continued

Polymers having at least one amine moiety.

| INCI name | structure |
|---|---|
| VP/dimethyl-aminoethyl methacrylate copolymer | (structure shown) |
| vinyl caprolactam/VP/dimethyl-aminoethyl methacrylate copolymer | (structure shown) |
| quaternized copolymer of VP and dimethyl-aminoethyl methacrylate | (structure shown) |
| copolymer of VP and methacryl-amidopropyl trimethyl-ammonium chloride | (structure shown) |
| VP/dimethyl-aminopropyl methacrylamide copolymer | (structure shown) |

TABLE 2-continued

Polymers having at least one amine moiety.

| INCI name | structure |
|---|---|
| polyquaternium-55 | 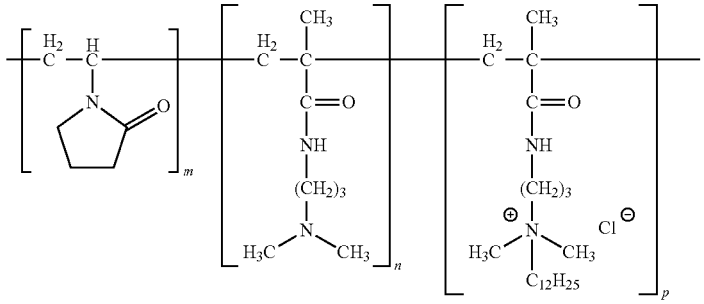 |
| polyquaternium-28 and dimethicone | 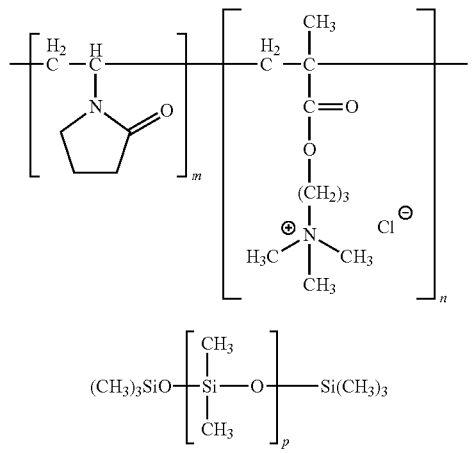 |
| polyquaternium-28 | 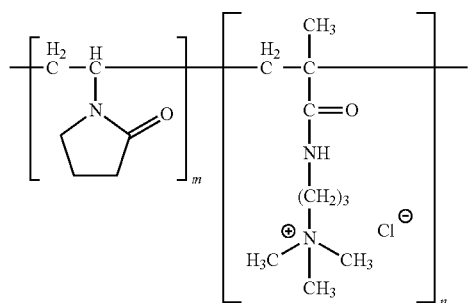 |
| polyquaternium-7 | 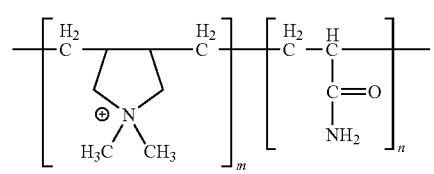 |

The following brochures related to the materials of Table 1 and 2 are hereby incorporated in their entirety by reference: *Personal Care Reference Guide*, International Specialty Products, 2009; *Aquaflex XL-30, A Volumizing Styling Resin with Long Lasting Hold*, May 2003; *RapiThix®, Versatile Rheology Modifiers for the Many Moves of Hair*, December 2004; *The Modern, Groomed Man, ASI Ingredient Applications for the Personal Care Market*, March 2006; *Guide For Color Cosmetics*, February 2006; *Stabileze® Versatile Rheology Modifier*, June 2005; *A Formulation Guide For Excellent Hair Styling Gels and Lotions*, April 2003; *Polymers For Oral Care, Product and Applications Guide*, April 2003; *Specialty Products for Personal Care, Gantrez® SP-215 A Polymer for "High Solids" Hairsprays* (no date); *Specialty Products for Personal Care, Gantrez® A-425 Resin For Soft To Hard Hold Hairspray Formulations* (no date); *Performance Enhancing Products for Personal Care, Gantrez® ES, SP Monoester Resins* (no date); *Specialty Products for Personal Care, Advantage® PLUS A New Hair Fixative Polymer* (no date); *ASI LabTalk™, Hair Care, Enhancing Shine of Styling Products*, January 2006; *Healthy Beautiful Hair, Serums are hot . . . Re-hydrate, Restructure, Revitalize, Renew & Protect, Innovative Product Applications* (no date); *ASI LabTalk™ Personal Care,*

*Advantage® S,* 2003; *Hair Care Formulation, Styleze® XT3 Durable Frizz Control Cream* (#12042-18A); *Hair Care Formulation, Styleze® XT3 Durable Frizz Control Mousse* (#12042-17); *Copolymer 845 & 937, Versatile Fixative Polymers for Styling Gels and Mousses,* May 2003; *Specialty Products for Personal Care, Gafquat® 734, 755N and HS-100 Cationic Conditioning Copolymers* (no date); *Specialty Products for Personal Care, Polymer-Silicone Encapsulates PVP/SI-10 and Gafquat® his for Hair and Skin Care* (no date); *Performance-Enhancing Products for Personal Care, Styleze™ CC-10 Climate control and Thermal Protection for hair* (no date); *ASI LabTalk™, Personal Care, Styleze 2000,* April 2004; *Performance-Enhancing Products for Personal Care, Styleze® W-20, A New Cationic Polymer For A Conditioning Hold Even in High Humidity* (no date); and *ASI LabTalk™, Hair Care, Split End Mending,* August 2004.

One non-limiting choice for this second compound of the invention is the polymer isobutylene/dimethylaminopropylmaleimide/ethoxylated maleimide/maleic acid (polyimide-1). This polymer features both an amine moiety and maleic acid/half-ester moieties, which also facilitates its chemical reactivity also as a first compound of the invention. For this example it is noted that the first and second compounds of the durable styling composition indeed can be a single, unitary compound.

Polyimide-1 and compounds based on it can be customized to offer unique and durable styling compositions. The parent polymer, polyimide-1, can be represented by the structure:

Suitable compounds having at least one amine moiety include polyether amines, such as the Jeffamine® product line offered for commercial sale by Huntsman Corporation (Everberg, BE). A review of this product line is presented in a published sales brochure titled, "The Jeffamine® Polyetheramines," which is incorporated herein in its entirety by reference. These polymers are primarily based on ethylene oxide (EO) and/or propylene oxide (PO), and contain one, two, or three primary amine groups per molecule.

A feature of the Jeffamine® polyether amines is the range of properties attainable by customizing the units, ratio of EO/PO, and molecular weight. For example, the Jeffamine® ED series possesses a polyethylene glycol-based backbone, and is completely water soluble, while various "experimental amines" are oleophilic and not water soluble. Hence, these polyether amines are contemplated singly and in combinations.

The Jeffamine® family of polymers also offers chemical flexibility by offering different numbers of amine groups per molecule, including (but are not limited to) polyether monoamines (e.g., Jeffamine® M series), polyether diamines (e.g., Jeffamine® D, ED, and EDR series) and polyether triamines (e.g., Jeffamine® T series). These different polymer families allow formulation and product flexibility while maintaining essentially the same base chemistry.

This discussion of polymer backbone chemistry and number of amine groups per molecule is not unique to the Jeffamine® family, as one skilled in the art will recognize that these details can extend to other related families as well.

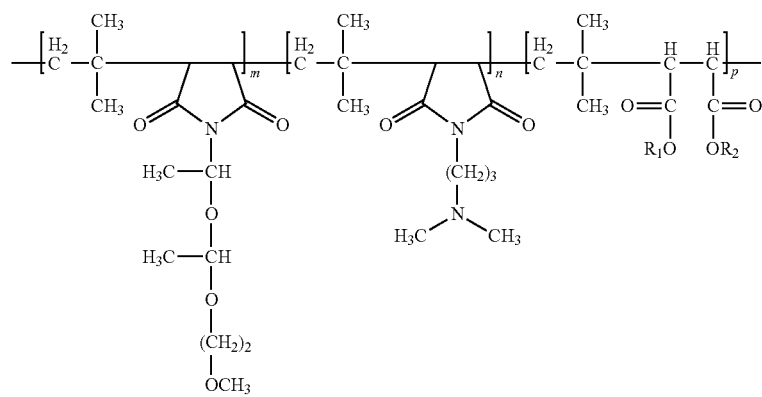

wherein the subscripts m, n, and p are represent the molar ratios of the three blocks that together add to 100%. As in the definition of structures (1) and (2), $R_1$ and $R_2$ are independently selected from the group consisting of: hydrogen, alkyl groups, alkali metals, and alkaline earth metals. During the polymerization process different amounts of monomers can be used, crafting polymer having more amine content (higher value of n) or more acid functionality (higher value of p). In fact, the inventors have discovered that polyimide-1 having high-acid content by itself contains sufficient levels of both the acid functionality and amine moiety so that a second acid- or amine-containing compound may, but does not have to be added.

In another embodiment, the second compound that comprises at least one second compound having at least one amine moiety or hydroxyl group is not a polymer. For example, the second compound may be an oligomer or a small molecule.

For example, polyethyleneimine is well known to those skilled in the art, and a description is provided in *Kirk-Othmer Encyclopedia of Chemical Technology,* third edition, volume 20, 1982, pages 214-216, which is incorporated herein by reference. The use of polyethyleneimines with primary and secondary amine functionality is contemplated. Linear, branched, and hyperbranched polyethyleneimines are commercially available from Polysciences, Inc. (Warrington, Pa.). Typical polyethyleneimine molecular weights range from about 1,200 g/mol to 100,000 g/mol, although polyethyleneimines with molecular weights outside this range are known to those skilled in the art.

Aminofunctional silicones represent another class of compounds that find application in this invention. Broadly speaking, these compounds contain at least one amine group and at least one silicon atom. They represent a broad array of chemistries. For example, aminoalkylsiloxanes, diaminoalkylsiloxanes, aminoalkoxysiloxanes are two non-limiting examples of this polymer family, which can be further reacted to yield chemistries that include polyimides, polyureas, and polyurethanes.

Examples of aminofunctional silicones include isostearamidopropyl dimethylamine gluconate (and) propylene glycol amine-functional silicones; offered for commercial sale by The Lubrizol Corporation (Wickliffe, Ohio). Also available are a number of aminopropyl-terminated polydimethylsiloxanes, N-ethylamino-isobutylterminated-polydimethylsiloxanes, aminopropylmethylsiloxane-dimethylsiloxane copolymers, aminoethyl-aminopropyl-methylsiloxane-dimethylsiloxane copolymers, aminoethyl-aminoisobutyl-methylsiloxane-dimethylsiloxane copolymers, and aminoethyl-aminopropylmethoxysiloxane-dimethylsiloxane copolymers, all of which are offered for commercial sale by Gelest, Inc. (Morrisville, Pa.). Combinations of these compounds having amine units also are contemplated.

Further examples of suitable amino polymers include, but are not limited to the amino polymers disclosed in U.S. Pat. Nos. 5,270,379; 5,373,052; 5,496,545; 5,624,963; 5,667,775; 5,679,717; 5,693,675; 5,703,188; 6,008,316; U.S. Patent Application 2009/0012241; international application WO 2008/066849, all of which are incorporated herein their entirety by reference.

Other functionalized analogues of these amine compounds may be employed, such as those containing other siloxane, silanes, quaternary moieties, and/or other functional groups known and used in the personal care arts.

Alternatively, the second compound having at least one amine moiety or hydroxyl group may be an amino acid, a protein, or combinations thereof. Examples of amino acids include: arginine, histidine, lysine, aspartic acid, glutamic acid, serine, threonine, asparagine, glutamine, cysteine, selenocysteine, proline, alanine, valine, isoleucine, leucine, methionine, phenylalanine, tyrosine, and tryptophan. Proteins may be recognized as being constructed at least in part from one or more of these amino acids.

The second compound having at least one second compound having at least one amine moiety or hydroxyl group may be any saccharide, or a blend of saccharides. The saccharide may be a monosaccharide, a disaccharide, a polysaccharide, or oligosaccharide. Non-limiting examples of saccharide units according to the present invention include erythrose, threose, arabinose, ribose, lysose, xylose, glucose, mannose, allose, altrose, talose, galactose, idose, gulose, fructose, and combinations thereof. For example, the saccharide can comprise two or more of these saccharide units, as in trehalose, which is formed by two glucose units.

The second compound having at least one second compound having at least one amine moiety or hydroxyl group may be any small molecule. For example, the small molecule may be any compound having at least one amine moiety and/or at least one hydroxyl group.

The compositions finding utility for creating a durable hair style typically will comprise at least one solvent-propellant for the first and second compounds. The term "solvent-propellant" refers to compounds that exhibit properties ranging from though of a solvent (solvency) to those of a propellant for contained systems. A propellant for contained systems may also act as a solvent or cosolvent for the other ingredients. Such solvent-propellants generally will be appropriate for the intended application, meaning the solvent-propellant will be non-irritating, non-toxic, compatible with other co-ingredients, and allow delivery of the final product form. Given these considerations, water and lower molecular weight alcohols, either alone or used in combination may be used. Additional benefits from their use is their low cost and commercial availability. Examples of lower molecular weight alcohols include ethanol, 1-propanol, 2-propanol, and n-butanol. It is recognized that in some jurisdictions methanol may be used to denature ethanol, and the use of methanol also is contemplated.

In other formulations, e.g., mousses or aerosols, the solvent-propellant may take the form of a propellant or liquefied gas, which include, but are not limited to: dimethyl ether, hydrofluorocarbon 152A, n-butane, isobutane, propane, isopentane, compressed air, liquefied nitrogen, nitrous oxide, liquefied carbon dioxide, and combinations thereof. Other suitable propellants and liquefied gases can be identified by one skilled in the art.

Different total solids levels can be attained based on the amount of solvent-propellant blended with the abovedescribed first and second compounds, and other optional ingredients. For example, durable styling compositions intended as a final product for consumer use may contain from 0.5% to 10% (w active/w) total solids. More particularly, these end-use durable styling compositions may contain from 2% to 6% (w/w) total solids. Lesser amounts of active solids also may be used, depending on the final product formulation and intended use(s).

More concentrated forms of the durable styling composition can be realized by a variety of approaches. These products at higher solids offer several benefits, like lower shipping and transportation costs, ease of storage since they occupy less volume, and the ability to reconstitute them to lower solids for end-use applications. First, and perhaps most simply, the solvent-propellant content can be reduced during preparation, thereby creating a durable styling composition of higher solids content. Alternatively, a durable styling composition can be prepared having a customary amount of solvent-propellant, which is then removed using any of the methods known in the art, such as distillation, vacuum distillation, belt drying, freeze drying, or spray drying methods. It is contemplated to pursue this approach to create formulations of very high solids levels, or even powders (i.e., 100% solids). Perry's Chemical Engineers' Handbook, Seventh Edition (1999) is a reference describing many of these methods, and is incorporated herein its entirety by reference.

The final solids level of a concentrated product may, in part, be determined by its viscosity. For example, the concentrate typically will be transferred into secondary containers for storage or shipping, and, hence, the viscosity must not be so great that the concentrate cannot be handled accordingly. A concentrate solids content from 10% to 50% (w/w) solids should be adequate for most formulations. In one aspect of this embodiment, the concentrate contains from 10% to 40% (w/w) solids. More particularly, the concentrated durable styling compositions may contain around 30% (w/w) solids, which may provide a satisfactory viscosity for storage and dilution capability.

Optional Ingredients

In addition to the required first and second compounds and solvent-propellant, the durable styling compositions may also contain optional ingredients that may assist in the delivery, stability, rheology, or final product aesthetics, like texture, spreadability, foam quality, fragrance or color. The myriad of optional ingredients may be chosen from that materials commonly used and known in the art, and include those compounds disclosed in research disclosures IPCOM 000128968D, available at http://priorartdatabase.com/IPCOM/000128968, and IPCOM 000109682D, available at http://priorartdatabase.com/IPCOM/000109682, both of which are incorporated herein their entirety by reference.

Four optional ingredients-polyols, preservatives, chelating agents, and crosslinkers-merit discussion due to the special utility the offer the invention's compositions. Each will be summarized briefly to acquaint the reader with them.

The first of these optional ingredients, polyols, have been discovered in separate embodiments of the invention to enhance hair shine and softness experienced by the consumer. Polyols are recognized as compounds having more than one hydroxyl group. Well known classes of polyols include diols and glycols (having two hydroxyl groups) and triols (having three hydroxyl groups). Without being bound by theory, it appears the hydroxyl groups of polyols participate in forming a matrix with hair, the first compound, and/or the second compound via a hydrogen bonding or other mechanism. Alternatively, the hydroxyl groups of the polyol may be covalently reacting with these first and second compounds, or even the chemistry of hair itself. Regardless of the theory, the benefits that can be provided by the polyol include: enhanced hair shine and softness. Examples of suitable polyols include, but are not limited to, propylene glycol, dipropylene glycol, butylene glycol, caprylyl glycol, and the compounds described earlier in this specification for the second compound having at least one hydroxyl group.

Preservatives also may be formulated into the durable styling compositions to achieve the usual benefits they confer, namely, reducing or eliminating bacterial, yeast, and mould growth. Suitable preservatives include paraben- and paraben-free preservatives that are known in the field, and may be used in the customary amounts. Preservatives may be especially useful when formulating concentrated versions of the durable styling compositions, which may be stored prior to dilution and consumer use.

While described individually, the optional polyol(s) and preservative(s) can actually be the same compound. Two examples are Optiphen® and Optiphen® Plus, which are preservatives having a diol, caprylyl glycol, as an ingredient. Thus, the use of these preservatives and others like them can help reduce antibacterial growth and simultaneously enhance durable styling benefits without increasing the formulation burden by incorporating a separate polyol.

Chelating agents represent a third optional ingredient that may be added to the invention's compositions. Chelation is the process by which metal ions are rendered unable to react with other elements or ions. Chelators assist compositions of the invention by reducing or eliminating the need to use deionized water in the formulation. When the first and second compounds in the durable styling composition are polymers, then chelating agents may help reduce the risk of polymer coagulation, the formation of precipitates or scale. The chelator may be a natural substance, like proteins or polysaccharides, or synthetic, like ethylenediaminetetraacetic acid or one of its salts, such as ethylenediaminetetraacetic tetrasodium (EDTA Na4).

Finally, the invention also provides for one or more optional initiators in the durable styling composition. The inventors discovered the addition of such materials can enhance the durable benefits of the invention's compositions and methods. Without being bound by theory, it appears the abovedescribed first compound (A) and second compound (B) share an interaction with each other and/or with hair (e.g., covalent bonding, hydrogen bonding, Van der Waal attraction) and form a matrix that is facilitated by the application of heat. Adding one or more initiators may assist this matrix formation, thereby increasing the interactions. Non-limiting examples of suitable crosslinkers include hydrogen peroxide, ceric complexes, ammonium persulfate, sodium persulfate, potassium persulfate, cumene peroxide, t-butylperoxypivalate, benzoyl peroxide, as well as mixtures of these initiators.

Other polyols, preservatives, chelating agents, and crosslinkers can be identified by one skilled in the art, for example, by referring to the infobase of the Personal Care Products Council and the Inventory and Common Nomenclature of Ingredients Employed in Cosmetic Products (dated 9 Feb. 2006), both of which are hereby incorporated herein their entirety by reference.

Durable Styling Benefits and Method

The durable styling compositions described above impart benefits that have not been known before. Unlike U.S. Pat. No. 6,241,977, which describes a method for protecting hair from thermal degradation, compositions described herein provide hair styling benefits that persist up to five wash (i.e., shampoo) cycles or more. Consumer benefits include shine, conditioning, defrizzing, decurling, decurling and/or dewaving (or curls and waves when imparting these styles to straight hair), waving, softness, ease of styling, volume improvement, dry combability, wet combability, smooth feeling, improved hair alignment, manageability, color protection, humidity resistance, or overall appearance when the invention's compositions are employed in the styling method.

In one embodiment, the method comprises applying the durable styling composition to hair that is to be treated. Generally speaking, any application amount suffices that covers the hair to be treated. In laboratory studies on tresses, an application level of about 0.15 g of durable styling composition per gram of tress hair was found to yield effective results. In practical use, higher levels may be used by the stylist or consumer, particularly to make it easier to apply the product. Lesser amounts may be used, for example, if only a section of hair, just the hair tips, or hair roots are to be treated. The consumer may prefer that the hair be shampooed and/or towel dried before this application. Also, it may be preferred that the hair be damp, as it may aide in the distribution of the durable styling composition, but dry hair also may be treated. For best results, the durable styling composition should be uniformly delivered, e.g., working from root end to hair tip. The composition may be left in the hair and not be completely removed by washing or rinsing. If the hair has been treated with an excess of composition, the hair may be lightly patted with a towel to absorb and surplus composition, or removed with the fingers.

At this point, the hair optionally may be combed or brushed to detangle the hair, which may also assist in the styling step which follows.

It is believed that the noted benefits are achieved by creating a crosslinked/bonded network of the first and second compounds to each other and to hair. (As described earlier, the first and second compounds according to the invention may be a single compound by itself, such as compounds like a polyimide-1 having high acid content.) One method of accomplishing this effect is by applying heat to the treated hair. As mentioned above, it is believed that the first-time heating initiates a dehydration reaction that convert structures (1) and (3) to the anhydride forms of structures (2) and (4). These groups, in turn, react with the amino acids in hair to form succinimide linkages between the hair and first compound. The exact temperature and duration of heat application depend on the formulation, as it was noted that half esters of maleic acid can dehydrate at lower temperatures than the diacid. In general, the hair styling temperature ranges from about 90° C. to 250° C. More particularly, durable styling may be attained using a temperature of about 130° C. to 230° C. Conventional, heated hair styling tools like flat-irons, curling iron, and hair dryers reach these temperatures, and are suitable for use. Flat-irons and curling irons offer unique hair styling possibilities, in that they can produce straight, curly, and/or wavy hair that, due to the durable styling composition, persists even after washing.

The heat application step may occur while the hair is wet/damp with the durable styling composition, or after it has dried (e.g., air dried, blow dried).

The invention also contemplates activating the durable styling composition by ultraviolet (UV) radiation, and other chemical initiators, such as hydrogen peroxide, ceric complexes, ammonium persulfate, sodium persulfate, potassium persulfate, cumene peroxide, t-butylperoxypivalate, benzoyl peroxide, as well as mixtures of these initiators.

After working the durable styling composition into the hair and applying heat, it is not necessary to reapply the composition nor heat to realize the hair styling benefits for up to five days afterward. The hair exhibits the noted benefits even after repeated washing cycles. Optionally, the consumer may wish to apply hair conditioner after washing and/or use styling products like creams, lotions, cream gels, pastes, waxes, hair sprays, mousses, and gels to assist with hair management, qualities, and/or styling preferences.

The compositions, methods, and benefits additionally are described by the following non-limiting examples:

EXAMPLES

Examples 1-96

Eighty-eight examples of the invention are prepared having a PVM/MA copolymer and polyimide-1 (Aquaflex® XL-30, 30% active); (Table 3, and Tables 4-11). For each choice of PVM/MA copolymer, 8 formulas are made. An acidic polymer solution with a pH of about 2 is produced after adding the PVM/MA copolymer to water. Under these very low pH conditions a complex results when polyimide-1 was added. In order to obtain a smooth solution of both polymers, the following procedure is followed: The PVM/MA copolymer is dissolved with about 40% of the water in a first vessel, after which the pH is adjusted to 3.5 using sodium hydroxide. In a second vessel the remaining water is mixed with the polyimide-1, and then this solution is added to contents of the first vessel. After mixing well the preservative (if any) is added the blended to yield a translucent, viscous polymeric solution. The selected preservative is a blend of phenoxyethanol and caprylyl glycol. The pH of the durable styling composition ranges from 3 to 7 to 11, although lower pH can be made for hair-straightening packs (e.g., for hot/flat irons) and higher pH of 12, 13, or even higher can be made for hair relaxers/wave treatments. Examples 89-96 were reduced to practice.

TABLE 3

Specification of the PVM/MA copolymer for Examples 1-96

| Example | PVM/MA copolymer | trade name |
|---|---|---|
| 1-8 | ethyl ester of PVM/MA copolymer in ethanol | Gantrez® SP-215 |
| 9-16 | | Gantrez® ES-225 |
| 17-24 | | Omnirez® 2000 |

TABLE 3-continued

Specification of the PVM/MA copolymer for Examples 1-96

| Example | PVM/MA copolymer | trade name |
|---|---|---|
| 25-32 | butyl ester of PVM/MA copolymer in ethanol | Gantrez® A-425 |
| 33-40 | | Gantrez® ES-425 |
| 41-48 | butyl ester of PVM/MA copolymer in isopropanol | Gantrez® ES-435 |
| 49-56 | isopropyl ester of PVM/MA copolymer in isopropanol | Gantrez® ES-335 |
| 57-64 | mixed sodium and calcium salt of PVM/MA copolymer (powder) | Gantrez® MS-955 |
| 65-72 | PVM/MA copolymer (powder) | Gantrez® AN-169 |
| 73-80 | | Gantrez® S |
| 81-88 | | Gantrez® S-95 |
| 89-96 | | Gantrez® S-97 |

TABLE 4

Formulas of Examples 1, 9, 17, 25, 33, 41, 49, 57, 65, 73, 81, and 89

| ingredient | addition level (% w/w) |
|---|---|
| water | 95.67 |
| PVM/MA copolymer (See Table 3) | 1.00 |
| polyimide-1 (Aquaflex® XL-30, ASI) | 3.33 |
| total | 100. |
| pH | 3 |
| | 7 |
| | 11 |

TABLE 5

Formulas of Examples 2, 10, 18, 26, 34, 42, 50, 58, 66, 74, 82, and 90

| ingredient | addition level (% w/w) |
|---|---|
| water | 96.50 |
| PVM/MA copolymer (See Table 3) | 1.00 |
| polyimide-1 (Aquaflex® XL-30, ASI) | 2.50 |
| total | 100. |

TABLE 6

Formulas of Examples 3, 11, 19, 27, 35, 43, 51, 59, 67, 75, 83, and 91

| ingredient | addition level (% w/w) |
|---|---|
| water | 97.34 |
| PVM/MA copolymer (See Table 3) | 1.00 |
| polyimide-1 (Aquaflex® XL-30, ASI) | 1.66 |
| total | 100. |
| pH | 3 |
| | 7 |
| | 11 |

TABLE 7

Formulas of Examples 4, 12, 20, 28, 36, 44, 52, 60, 68, 76, 84, and 92

| ingredient | addition level (% w/w) |
|---|---|
| water | 98.17 |
| PVM/MA copolymer (See Table 3) | 1.00 |
| polyimide-1 (Aquaflex ® XL-30, ASI) | 0.83 |
| total | 100. |

TABLE 8

Formulas of Examples 5, 13, 21, 29, 37, 45, 53, 61, 69, 77, 85, and 93

| ingredient | addition level (% w/w) |
|---|---|
| water | 95.92 |
| PVM/MA copolymer (See Table 3) | 0.75 |
| polyimide-1 (Aquaflex ® XL-30, ASI) | 3.33 |
| total | 100. |

TABLE 9

Formulas of Examples 6, 14, 22, 30, 38, 46, 54, 62, 70, 78, 86, and 94

| ingredient | addition level (% w/w) |
|---|---|
| water | 96.17 |
| PVM/MA copolymer (See Table 3) | 0.5 |
| polyimide-1 (Aquaflex ® XL-30, ASI) | 3.33 |
| total | 100. |
| pH | 3 |
| | 7 |
| | 11 |

TABLE 10

Formulas of Examples 7, 15, 23, 31, 39, 47, 55, 63, 71, 79, 87, and 95

| ingredient | addition level (% w/w) |
|---|---|
| water | 96.42 |
| PVM/MA copolymer (See Table 3) | 0.25 |
| polyimide-1 (Aquaflex ® XL-30, ASI) | 3.33 |
| total | 100. |

TABLE 11

Formulas of Examples 8, 16, 24, 32, 40, 48, 56, 64, 72, 80, 88, and 96

| ingredient | addition level (% w/w) |
|---|---|
| water | 93.92 |
| PVM/MA copolymer (See Table 3) | 2.00 |
| polyimide-1 (Aquaflex ® XL-30, ASI) | 3.33 |
| phenoxyethanol and caprylyl glycol (Optiphen ®, ASI) | 0.75 |
| total | 100. |

Example 97-192

Concentrated versions of Examples 1-96 are made to 22.5% (w/w) total solids (Table 12). The choice of PVM/MA copolymer follows the same sequence as in the examples above. First, tetrasodium ethylenediaminetetraacetic acid EDTA $Na_4$ is added to the water with mixing until uniform. Then, the PVM/MA copolymer is dispersed into the water with good mixing. The pH is adjusted with 50% NaOH solution to pH of about 4.5 before adding the polyimide-1, which is mixed-in until uniform. The caprylyl glycol and phenoxyethanol/caprylyl glycol are added individually, mixing until uniform. Once the mixture is uniform, the pH was adjusted to 7.1±0.2 with NaOH solution. Example 192 with Gantrez® S-97 was reduced to practice.

TABLE 12

Concentrated formulations of Example 97-192

| ingredient | addition level (% w/w) |
|---|---|
| water | 45.85 |
| EDTA $Na_4$ (Versene ® 100, Dow) | 0.75 |
| PVM/MA copolymer | 15.00 |
| polyimide-1 (Aquaflex ® XL-30, ASI) | 25.00 |
| caprylyl glycol | 1.90 |
| phenoxyethanol and caprylyl glycol (Optiphen ®, ASI) | 1.50 |
| NaOH (50% solution) | 10.00 |
| total | 100.00 |

Example 193-288

Concentrated versions for the formulation of Examples 1-96 are prepared at 30% (w/w) solids (Table 13). The choice of PVM/MA copolymer follows the same sequence as in the examples above. EDTA $Na_4$ is added at 1.00% (w/w) as a chelating agent for metal ions. The pH of this concentrate is adjusted to 7.9±0.2 by the addition of 11.1 grams of sodium hydroxide (50% solution) for every 100 grams of concentrate. Example 288 with Gantrez® S-97 was reduced to practice.

TABLE 13

Concentrated formulations of Examples 193-288

| ingredient | addition level (% w/w) |
|---|---|
| water | 38.20 |
| EDTA $Na_4$ (Versene ® 100, Dow) | 1.00 |
| PVM/MA copolymer | 20.00 |
| polyimide-1 (Aquaflex ® XL-30, ASI) | 33.30 |
| phenoxyethanol and caprylyl glycol (Optiphen ®, ASI) | 7.50 |
| total | 100.00 |

Example 289

Figure 2A:
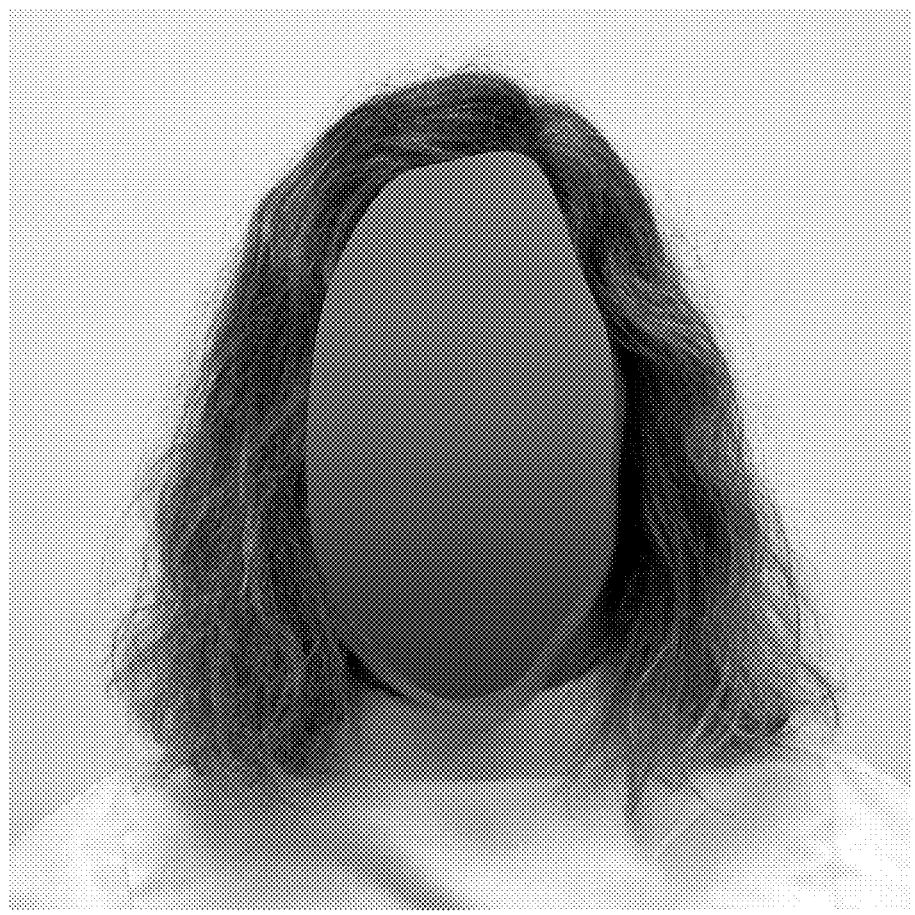
FIG. 2A-2C are photographs of hair treated in accordance with Example 289.

The formula from Example 96 was applied to the hair of two volunteer panelists. Both panelists had naturally curly hair (FIGS. 1A and 2A). The formula was applied by a licensed cosmetologist after washing the hair with a mild, commercial, non-conditioning shampoo, and then towel dried to remove excess water. The sufficient amount of the formula was used to saturate all hair from root ends to hair tips. The polymer solution was left on the hair, blow dried straight, and then the hair flat-ironed using a two-pass method to ensure hair reached the proper temperature for activating the durable styling composition.

Figure 1B:
Figure 2B:
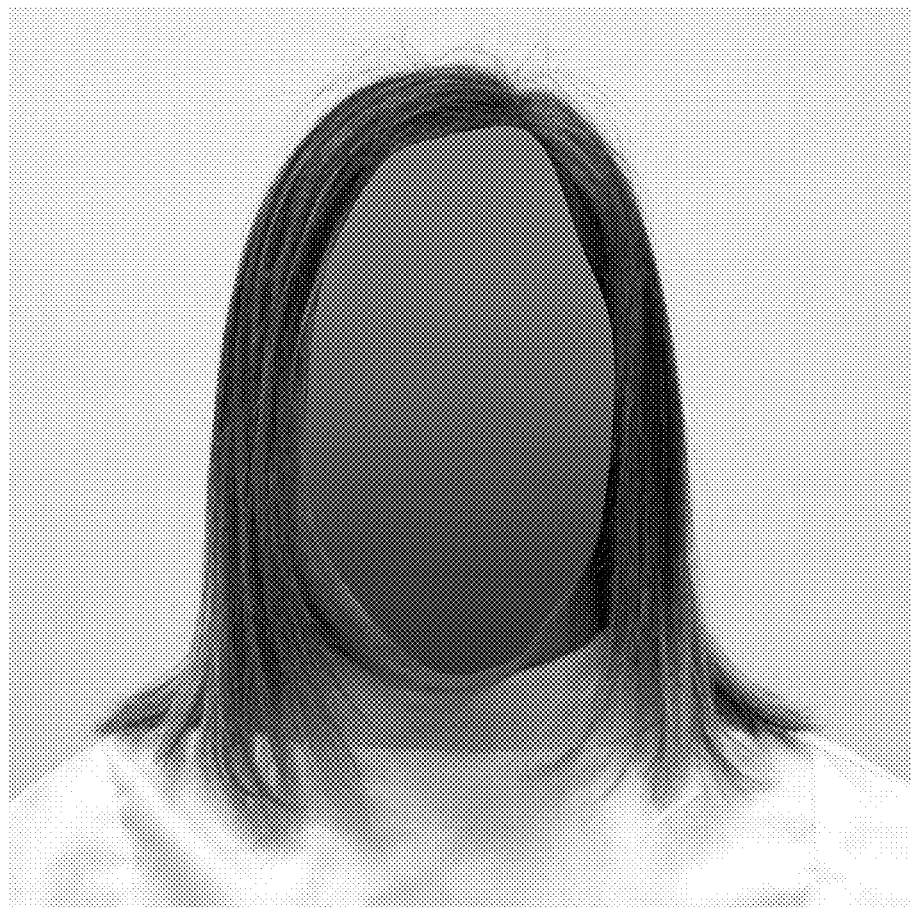

After treatment, both panelists had soft, straight, silky hair that appeared noticeably longer than the initial, curly hair (FIGS. 1B and 2B).

The panelists complied with the study request not to wash their hair, nor to apply any products to their hair (such as hair spray, gel, conditioner, or mousse) for 5 days. They were permitted to comb/brush their hair as needed. Instead, for days 2 through 5 the panelists returned to the licensed cosmetologist once a day who washed their hair using the same mild, commercial, non-conditioning shampoo, followed by a rinse-off conditioner, and towel drying. The hair was diffused-dried with a hair dryer, and then combed with a large-toothed comb. However, heated styling devices like a flat-iron or curling iron were not used.

Figure 1C:
Figure 1D:
Figure 2C:
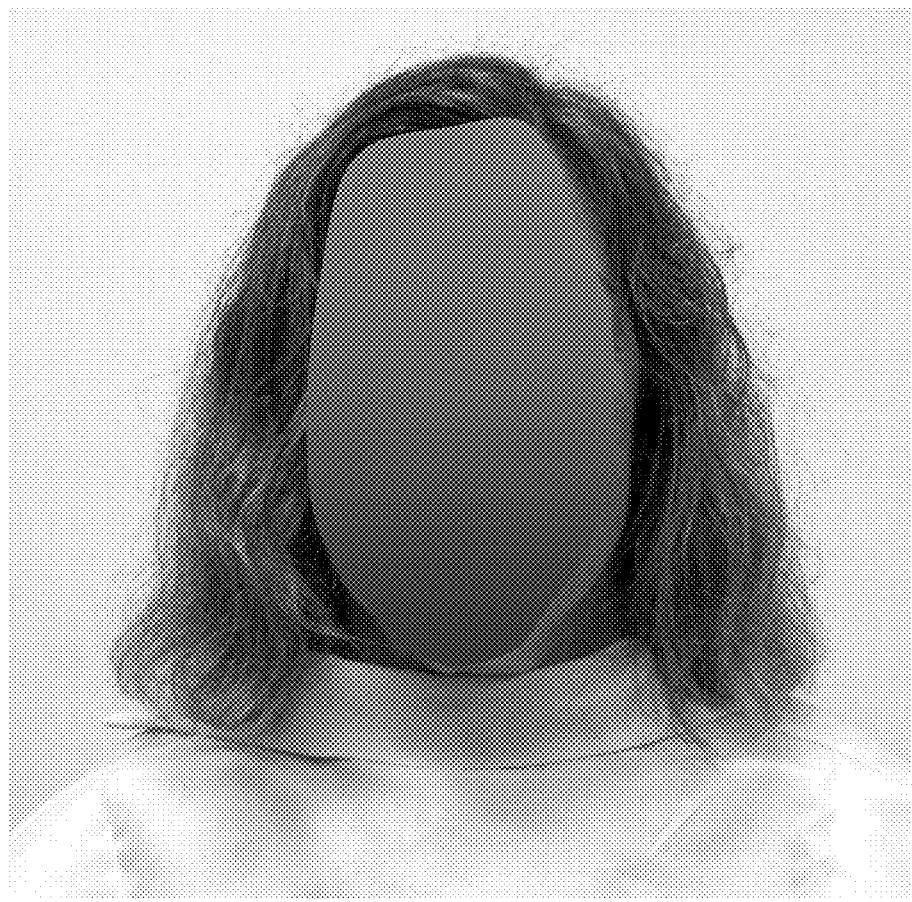

Like the experience after day 1, the panelists' hair retained a straight, silky appearance after day 3 (FIGS. 1C and 2C) and day 5 (FIG. 1D). Their hair maintained a sleek appearance, without the added hair volume defined by the initial waves, curls, or frizz. The panelists commented their hair felt very soft throughout the 5-day test period. Additionally, they said the test formula saved them considerable time since flat-ironing was not needed for their straight, freely-flowing hair style.

Comparative Example 1

One panelists participated in a comparative study wherein the cosmetologist identically followed the methodology described in Example 289, except after hair washing on day 1 no test formula (or any formula) was applied to the damp hair.

Figure 3:
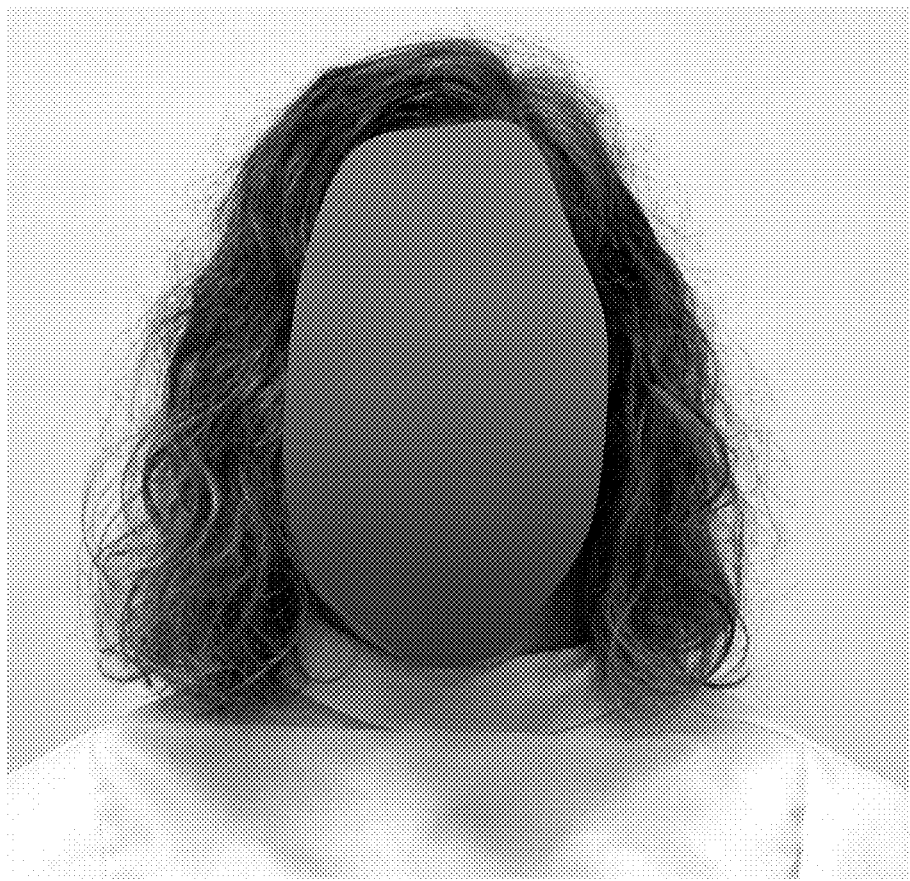
FIG. 3 is a photograph of hair treated in accordance with Comparative Example 1.

After day 3 her hair treated in this placebo manner exhibited the same amount of curl and hair volume (FIG. 3) as before treatment (FIG. 2A).

Example 290

A hair lock was divided into three equal tresses in order to evaluate the effect of three treatments on frizz. The first and second tresses served as controls, while the third tress was treated in accordance with the invention. Each tress was equally washed with a non-care/non-conditioning shampoo, and then rinsed until the water was clear. The first hair tress was blow dried straight and then flat ironed using 4 passes with a flat iron at a setting of 232° C. and a rate of 1.25 inch per second. The second tress received a commercially-available, frizz-control hair product, which was applied while the tress was damp (as recommended on the package), and then blow dried straight. The formula of Example 288 was applied to the third (damp) tress at the use level of about 0.3 gram of formula per gram of hair. This formula was not rinsed off the third tress (i.e., it was left in), and the tress was blow dried straight and flat ironed using the same method as described for the first tress. The tresses were stored together at 27° C. and 90% RH. To assess the amount of hair frizz, tress width was measured every ½ inch along the entire hair tress length, and then averaged. Width measurements were made immediately after treatment, and then after 2 and 4 hours of storage.

Figure 4:
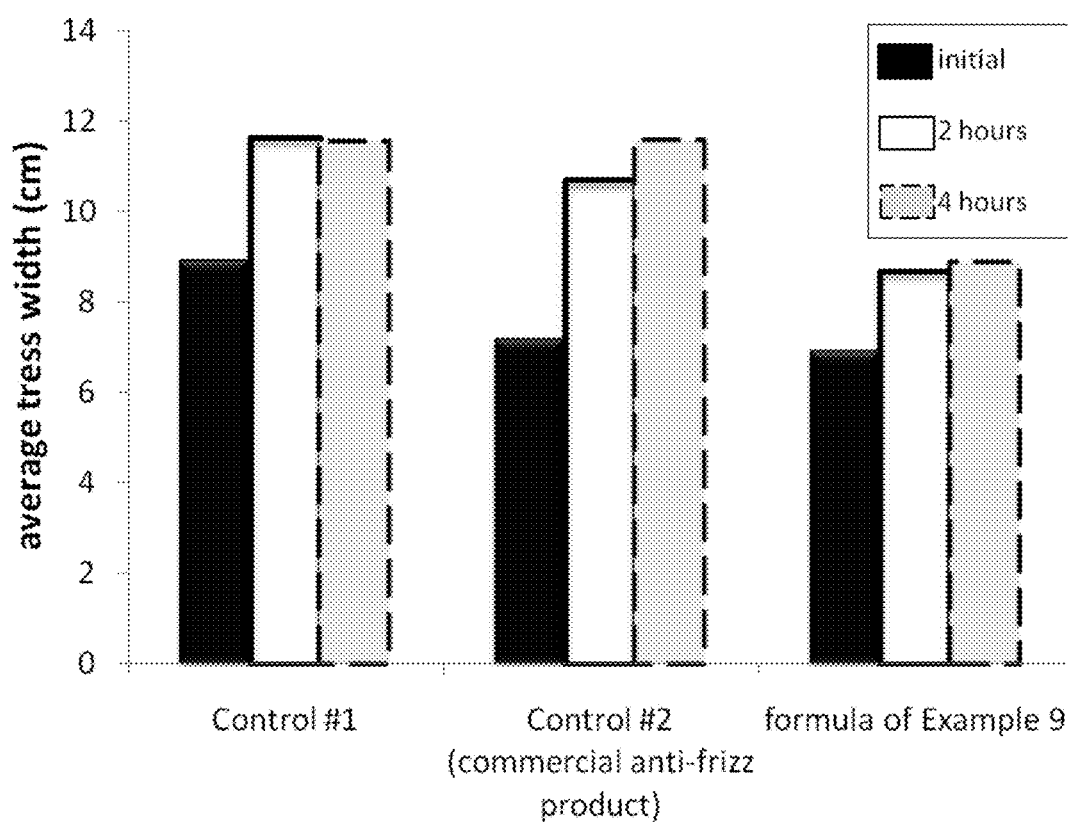
FIG. 4 is a bar graph of average tress widths for tress samples in accordance with Example 290.

Although all tresses were from the same initial hair lock, the third tress (treated in accordance with the invention) showed better initial frizz control than either control tress, as illustrated by a narrower average width (FIG. 4). After 2 and 4 hours of high temperature and humidity exposure, the third tress better resisted frizz gain than either control. In fact, after 4 hours the third tress remained exhibited a narrower width (less frizz gain) than the tress that was not treated with a frizz product (Control #1).

Example 291

The formula and method of Example 289 were substantially repeated with 9 different volunteer panelists. The licensed cosmetologist evaluated each panelists' initial in both the dry and wet stages. Then, she re-evaluated the dry and wet hair after treating with the durable styling composition, and then after the subsequent third, and fifth in-salon washes. The parameters included in her dry hair evaluation were: dry combability, smooth feel, anti-frizz, shine, manageability, decurling, and overall appearance. Likewise, the wet hair parameters of her evaluation were wet combability, smooth feel, and clean feel. For each property a number from 1 to 5 was assigned.

Figure 5:
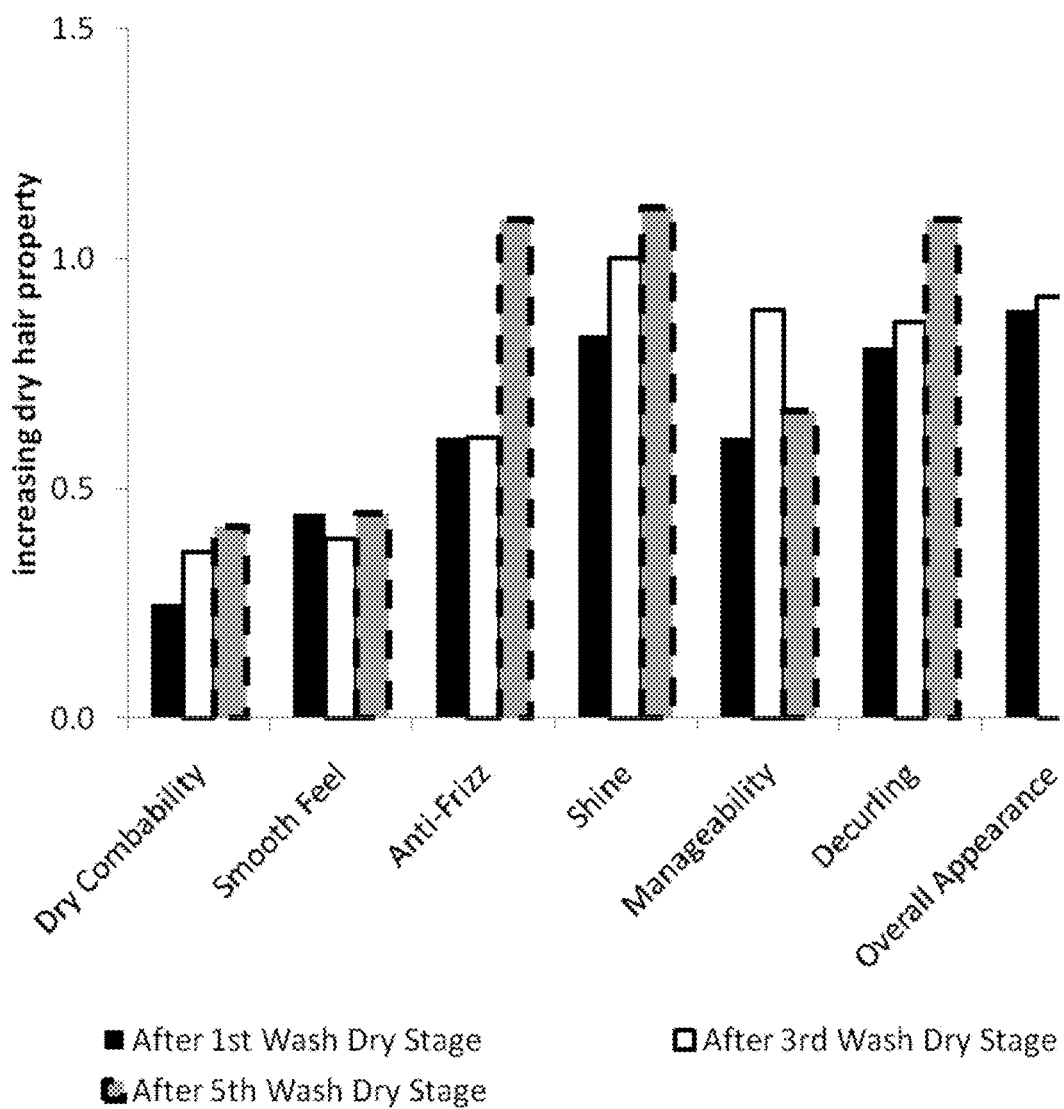
FIG. 5 is a bar graph of dry hair properties as described in accordance with Example 291.

The durable styling composition enhanced all of the dry hair properties (FIG. 5). Of special note, the treatment improved the anti-frizz, shine, manageability, visible curl pattern, and overall appearance qualities of dry hair, particularly after the fifth in-salon washing. Panelists further commented their hair felt very soft, displayed good body, and showed improved alignment. One panelist expressed satisfaction that upon waking her hair still looked neatly styled and picture perfect.

Figure 6:
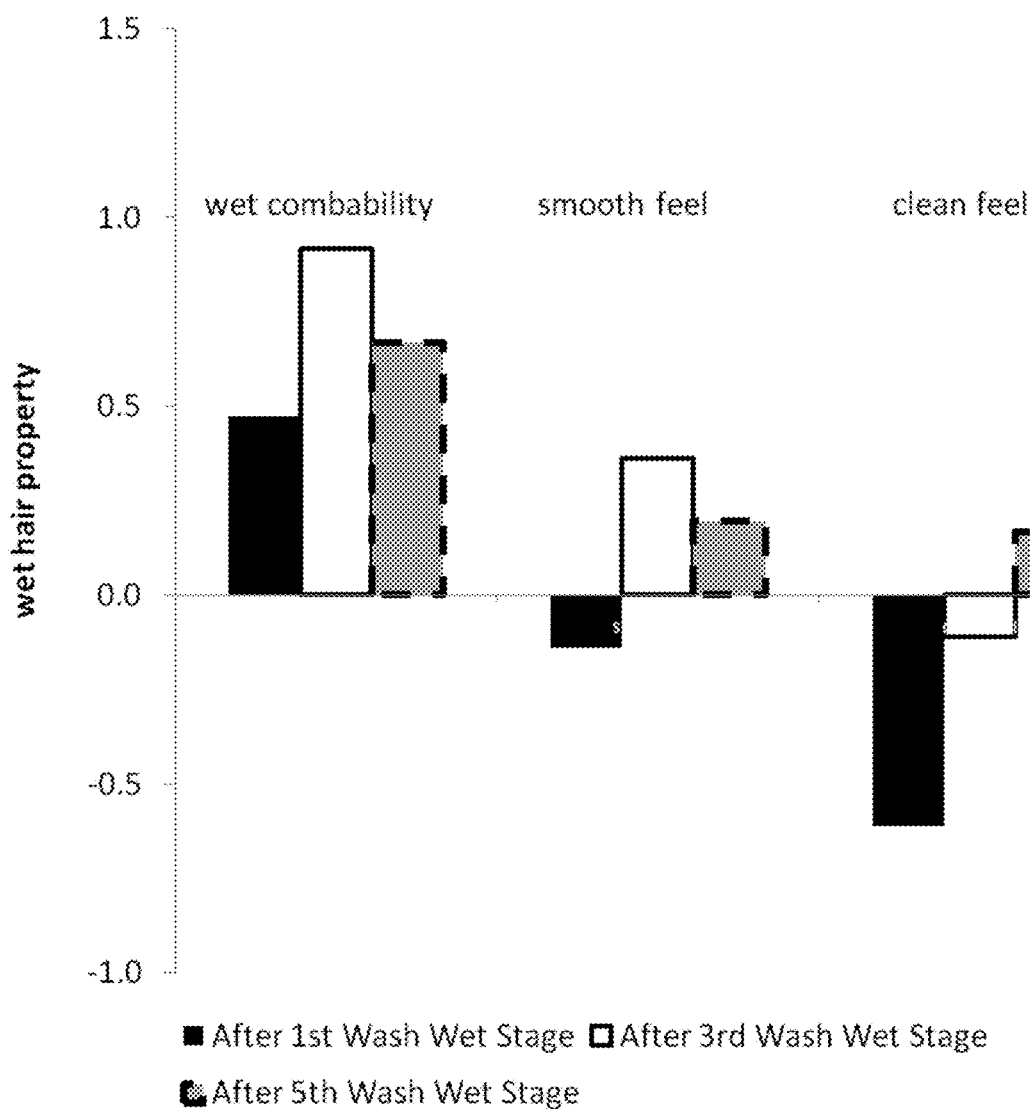
FIG. 6 is a bar graph of wet hair properties as described in accordance with Example 291.
Figure 7:
FIG. 7 is a photograph of a tress treated in accordance with Example 292.
Figure 8:
FIG. 8 is a photograph of a tress treated in accordance with Example 292.
Figure 9:
FIG. 9 is a photograph of a tress treated in accordance with Example 292.
Figure 10:
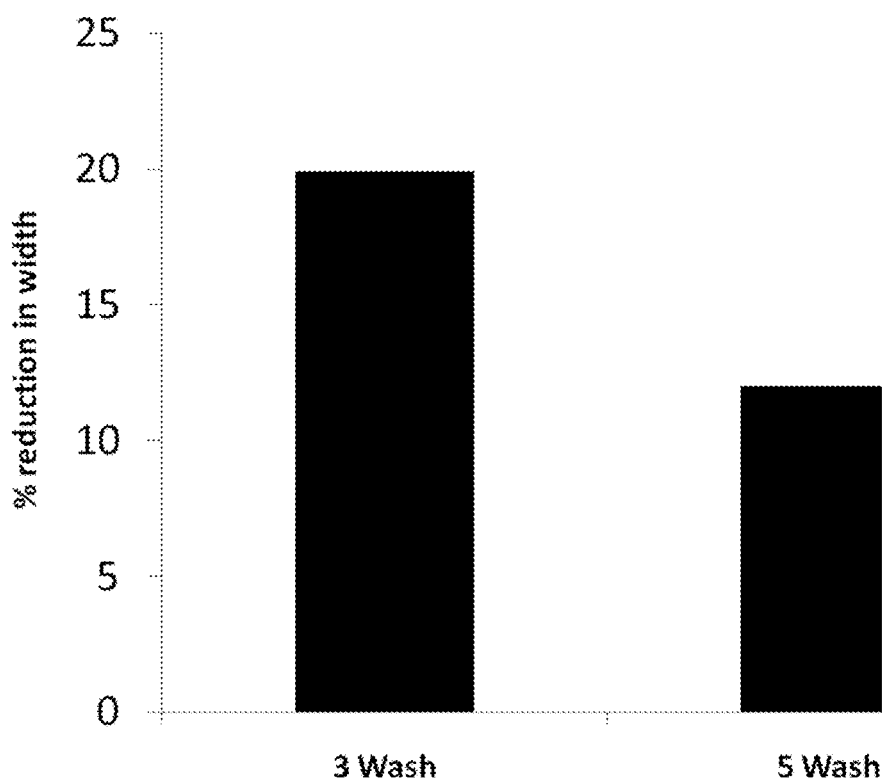
FIG. 10 is a graph of reduction in width as a function of number of washes for tresses treated in accordance with Example 292.

Similarly, the durable styling treatment provided an improvement in wet combability (FIG. 6).

Example 292

The formula of Example 96 was applied to curly hair tresses by the following procedure: First, the tresses were prepared by rinsing in water, shampooing, and then rinsing in fresh water, each step lasting 1 minute. Then, the tresses were treated by working 0.5 g to 1.0 g of test formula on the tress for 15 seconds. Tresses were detangled using a large-toothed comb, and then clipped into a vertical clamp. A hair dryer on "high" and "hot" setting was applied for about 1 minute, 20 seconds to dry the tresses. Then, the tress clamps were turned horizontal and straightened at 200° C. using 4 strokes from a large-toothed comb at the rate of 1 stroke every 5 seconds.

For days 2 through 5 the tresses again were rinsed, shampooed, and rinsed, and then a conditioner was applied, followed by a final rinse in clean water, each step lasting 30 seconds. Tresses were dried by placing under a dome hair dryer for 1 hour.

The tresses were analyzed using two methods. By the first method, tress widths were measured by placing them in front of a vertical grid having half-inch marks. Compared to the pre-treated tress width, the tress was 20% and 13% narrower after days 3 and 5, respectively (FIG. 7-10), an effect attributed to the durable straightening/defrizzing/decurling of the original curly hair. A second technique was employed to help understand how the invention affects hair shine and manageability. In this method the tresses were analyzed by measuring luminosity as a function of the distance from the anchoring clamp. This method quantified both hair shine (i.e., magnitude of luminosity) and hair manageability (i.e., period of the luminosity peak), as well-aligned hair produces smaller periods of luminosity.

Figure 11A:
FIG. 11A is a photograph of tress treated in accordance with Example 292.
Figure 11B:
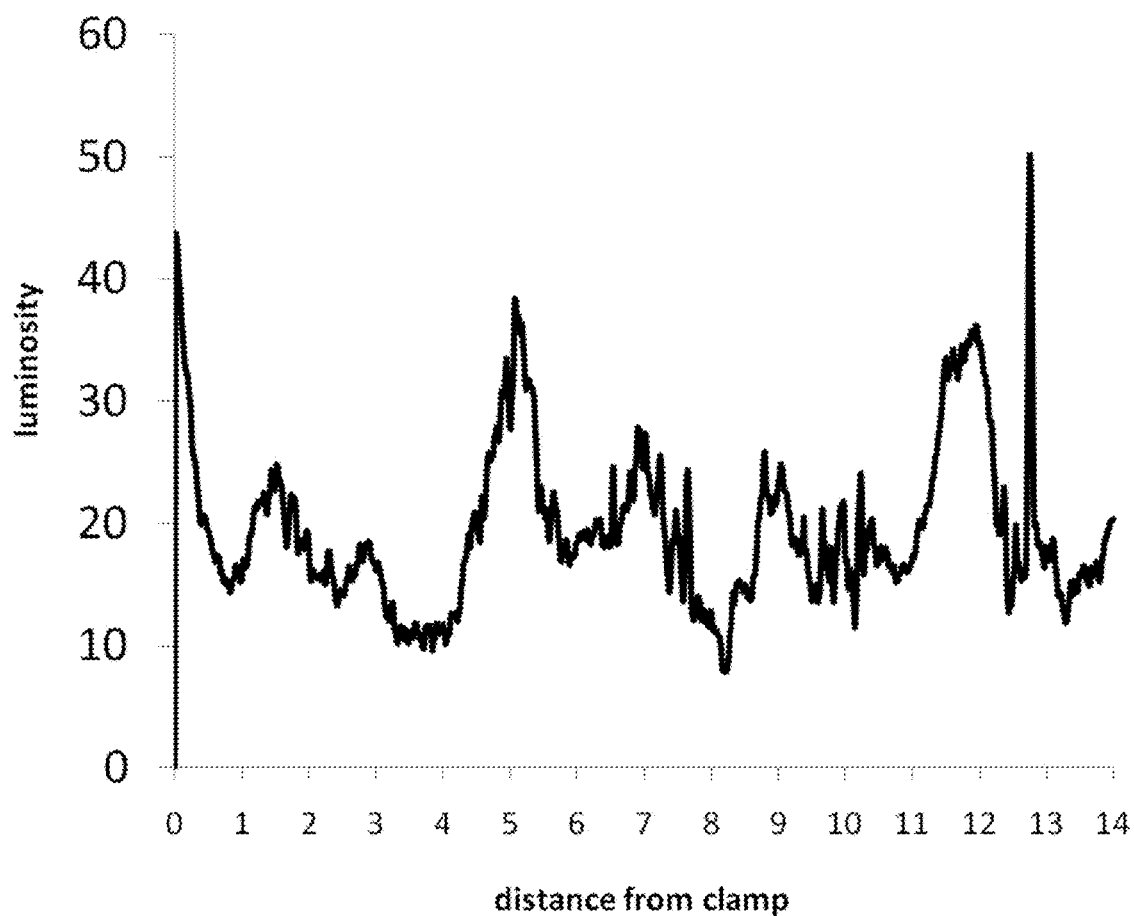
FIG. 11B is a luminosity graph for the tress of FIG. 11A.
Figure 12A:
FIG. 12A is a photograph of tress treated in accordance with Example 292.
Figure 12B:
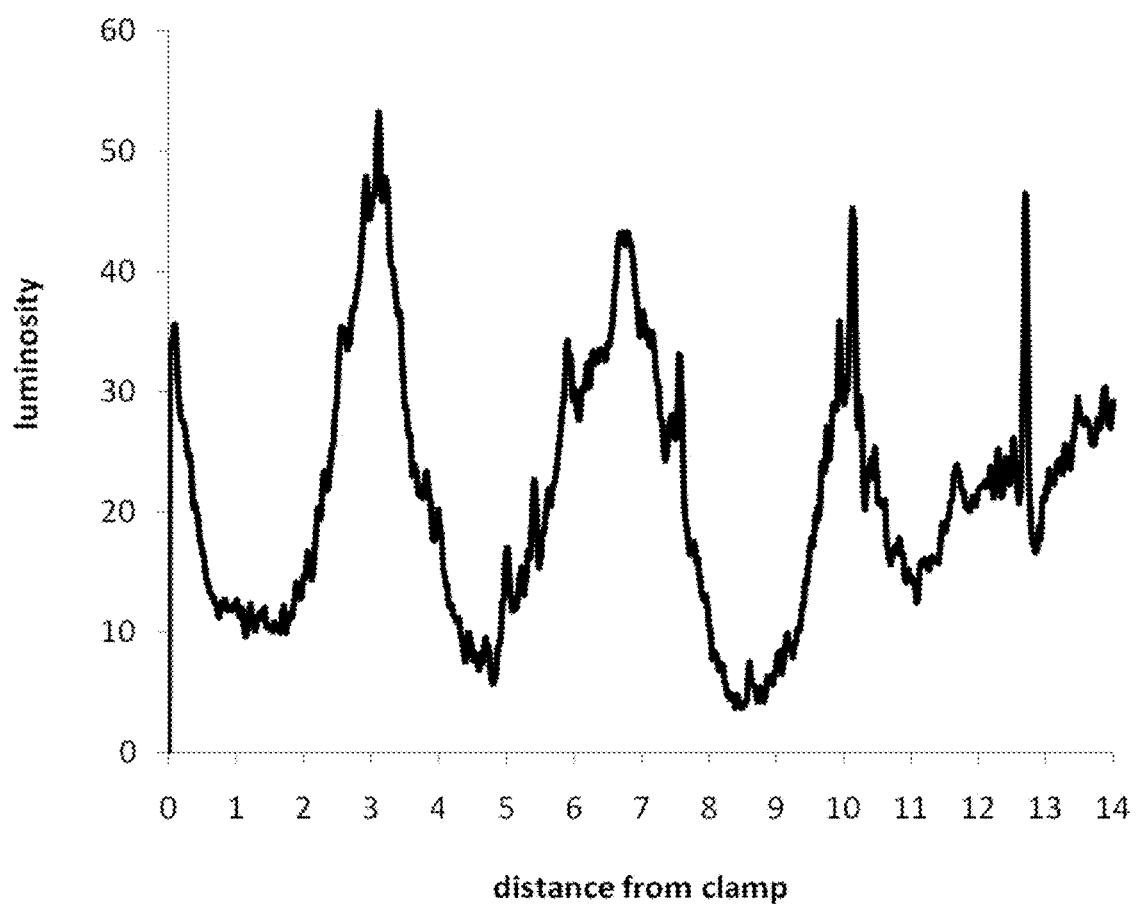
FIG. 12B is a luminosity graph for the tress of FIG. 12A.

Compared to the pre-treatment measurement (FIGS. 11A and 11B), hair is noticeably shinier after day 3, and the hair is highly aligned (FIGS. 12A and 12B).

Example 293

A composition of the invention was prepared having the formula summarized in Table 14.

TABLE 14

The formula of Example 293

| ingredient | trade name | weight addition (%) |
|---|---|---|
| deionized water | | 38.17 |
| ethanol | | 18.00 |
| ethyl ester of PVM/MA copolymer | Omnirez ® 2000, 50% active | 4.00 |
| sodium hydroxide | | 1.00 |
| polyimide-1 | Aquaflex ® XL-30, 30% active | 3.33 |
| butylene glycol | | 0.50 |
| dimethyl ether | | 35.00 |
| total | | 100.00 |

Example 294

A composition of the invention was prepared having the formula summarized in Table 15.

TABLE 15

The formula of Example 294.

| ingredient | trade name | weight addition (%) |
|---|---|---|
| deionized water | | 13.29 |
| ethanol | | 53.00 |
| sodium hydroxide | | to pH = 8 |
| VA/butyl maleate/isobornyl acrylate copolymer | Advantage ® PLUS, 50% active | 4.00 |
| sodium hydroxide | | 4.39 |
| polyimide-1 | Aquaflex ® XL-30, 30% active | 3.33 |
| butylene glycol | | 0.5 |
| hydrofluorocarbon 152A | | 21.50 |
| total | | 100.00 |

Example 295

Two compositions of the invention were prepared having the formulas summarized in Table 16.

TABLE 16

The formulas of Example 295

| ingredient | weight addition (%) | |
|---|---|---|
| | 12042-15-A | 12042-15-B |
| deionized water | 93.67 | 93.67 |
| PVM/MA decadiene crosspolymer (Stabileze ® 06/QM, 100% active) | 2.0 | 1.0 |
| PVM/MA copolymer (Gantrez ® S-97, 100% active) | 0 | 1.0 |
| sodium hydroxide (10%) | to pH = 7 | to pH = 7 |
| polyimide-1 (Aquaflex ® XL-30, 30% active) | 3.33 | 3.33 |
| phenoxyethanol (and) caprylyl glycol (Optiphen ®, 100% active) | 1.0 | 1.0 |
| total | 100.00 | 100.00 |

Examples 296-299

Four compositions of the invention were prepared using functionalized analogues of polyimide-1 (Table 17). The formulas were applied to tresses using the method of Example 289.

On average, tresses were longer three days after treatment than the original length and were less wide (Table 17), an indication that the initial hair frizziness was tamed and hair became more manageable.

TABLE 17

The formulas of Examples 296-299

| ingredient | weight addition (%) | | | |
|---|---|---|---|---|
| | 296 | 297 | 298 | 299 |
| deionized water | 84.95 | 89.45 | 80.93 | 87.68 |
| PVM/MA copolymer (Gantrez ® S-97, 100% active) | 2.00 | 2.00 | 0 | 0 |
| sodium hydroxide (10%) | to pH = 6 | to pH = 6 | to pH = 8 | to pH = 8 |
| polyimide-1 modified to high maleic acid (high acid) content (8.3% active) | 12.05 | 0 | 18.07 | 0 |
| polyimide-1 modified to highdimethylaminopropyl maleimide (high amine) molar content (13.2% active) | 0 | 7.55 | 0 | 11.32 |
| sodium hydroxide (10%) | to pH = 8 | to pH = 8 | to pH = 8 | to pH = 8 |
| phenoxyethanol (and) caprylyl glycol (Optiphen ®, 100% active) | 1.00 | 1.00 | 1.00 | 1.00 |
| total | 100.00 | 100.00 | 100.00 | 100.00 |

Examples 300-303

Four compositions of the invention are prepared using functionalized analogues of polyimide-1 (Table 18).

TABLE 18

The formulas of Examples 300-303

| ingredient | weight addition (%) | | | |
|---|---|---|---|---|
| | 300 | 301 | 302 | 303 |
| deionized water | 84.95 | 89.45 | 80.93 | 87.68 |
| PVM/MA copolymer (Gantrez ® AN-169, 100% active) | 2.00 | 2.00 | 0 | 0 |
| sodium hydroxide (10%) | to pH = 6 | to pH = 6 | to pH = 8 | to pH = 8 |
| polyimide-1 modified to high maleic acid (high acid) content (8.3% active) | 12.05 | 0 | 18.07 | 0 |
| polyimide-1 modified to high dimethylaminopropyl maleimide (high amine) molar content (13.2% active) | 0 | 7.55 | 0 | 11.32 |
| sodium hydroxide (10%) | to pH = 8 | to pH = 8 | to pH = 8 | to pH = 8 |
| phenoxyethanol (and) caprylyl glycol (Optiphen ®, 100% active) | 1.00 | 1.00 | 1.00 | 1.00 |
| total | 100.00 | 100.00 | 100.00 | 100.00 |

Example 304

Figure 13A:
FIG. 13A is a photograph of a tress treated in accordance with Example 304.
Figure 13B:
FIG. 13B is a photograph of a tress treated in accordance with Example 304.

The formula of Example 192 was applied to a straight hair tress (i.e., lacking curl, wave, or frizz), and the method of Example 289 was repeated. A curling iron set to "high" was employed to activate the durable styling composition and impart five curls into the tress (FIG. 13A). After 1 day the tress was washed and dried using the method described in Example 289. Waves persisted in the tress after washing, and distinct hair segments corresponding to the original curls were still discernible (FIG. 13B).

Example 305

An aspect of color protection was studied in this example. A single lock of hair was dyed red following the product's instructions. This dyed lock was rinsed for 30 seconds in clear, running water, shampooed using a non-care/non-conditioning shampoo for 30 seconds, and then rinsed for 30 seconds in clear, running water. Then it was divided into two equal hair tresses. The first tress (the control for the study) was dome dried after the shampoo rinse, and then the rinse/shampoo/rinse/dome dry cycle was repeated exactly as described for the original lock. The second tress received one gram of the Example 192 formula (diluted to 3% solids in water) while it was still damp after the first shampoo rinse. Excess formula was removed from the tress with the fingers, and then the tress was blow dried straight. Afterward, it was flat-ironed at 230° C. using 4 passes at 5-6 seconds per pass, allowed to equilibrate for 30 minutes at room temperature and humidity, and then rinsed/shampooed/rinsed/dome dried exactly performed before. Following the approach of M. Minguet, et al. ("Behenamidopropyl dimethylamine: unique behaviour in solution and in hair car formulations," *Int. J. Cos. Sci.*, 2010, 32, 246-257) and U.S. patent application 2010/0047201 (both of which are incorporated herein their entirety by reference), color retention of the dyed tresses was quantified using the color intensity ΔE*, using CIE L*, a*, b* color parameters measured by a Hunter Colorimeter Ultrascan Pro. The ΔE* values after the third, sixth, and tenth rinse/wash/dry cycles were relative to the initial, dyed hair lock.

Figure 14:
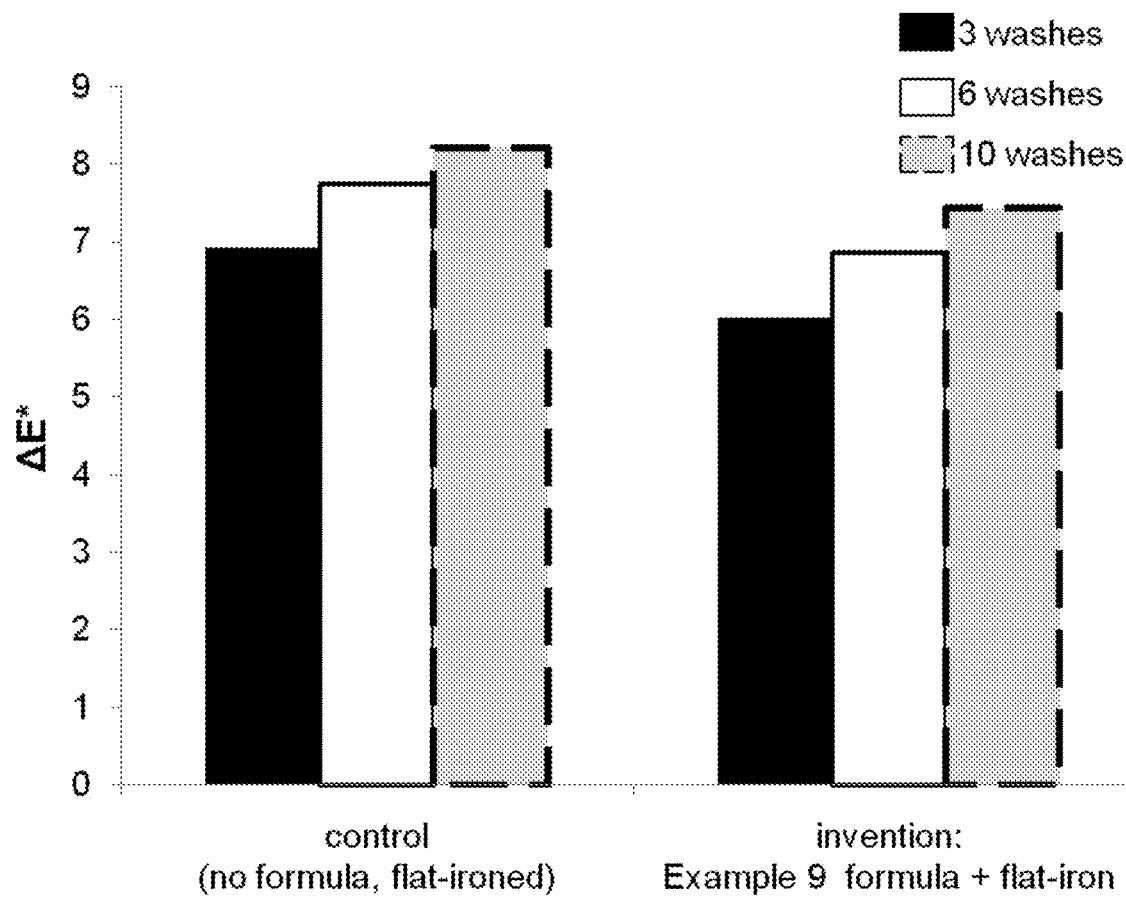
FIG. 14 is a bar graph of ΔE* for tresses treated in accordance with Example 305.

The formula of the invention gave lower values of ΔE* after the third, sixth, and tenth rinse/wash/dry cycles (FIG. 14), indicating that dyed hair treated according to the invention more closely resembled the original color than the no-formula control.

Example 306

Dynamic vapor sorption (DVS) studies were completed to assess the water sorptivity of hair treated in accordance with the invention. The sorption dynamics of brown, European hair were measured at 25° C. and 95% RH by a DVS Advantage I (Surface Measurement Systems, Middlesex, UK). The hair lock was rinsed for 30 seconds in clear, running water, shampooed using a non-care/non-conditioning shampoo for 30 seconds, and then rinsed for 30 seconds in clear, running water, and then dome dried. The lock was divided into two equal tresses. The control samples was analyzed without any formula or heat treatment. The other lock sample received one gram of the Example 192 formula (diluted to 3% solids in water) while it was still damp after the shampoo rinse. Excess formula was removed from the tress with the fingers, and then the tress was blow dried straight. Afterward, it was flat-ironed at 230° C. using 4 passes at 5-6 seconds per pass, allowed to equilibrate for 30 minutes at room temperature and humidity.

Figure 15:
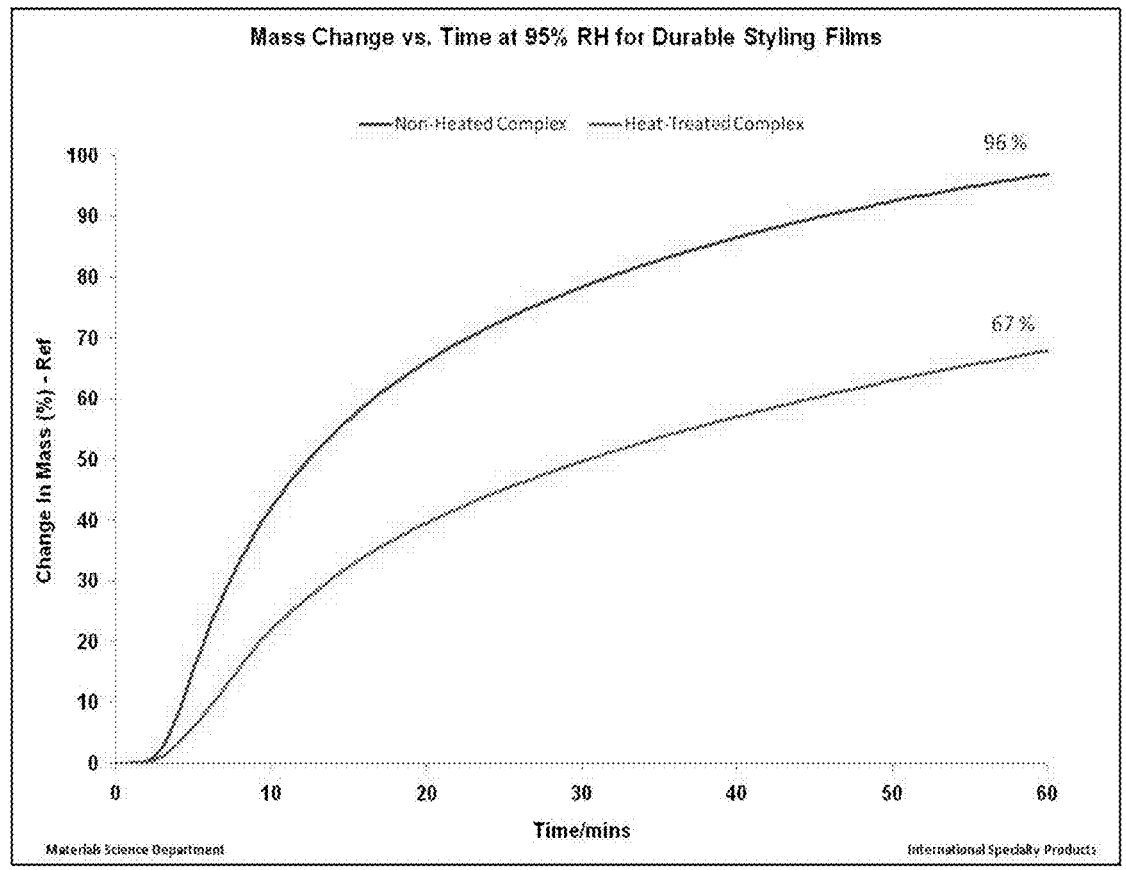
FIG. 15 is a graph of % mass change as a function of time for tresses treated in accordance with Example 306.

Following 60 minutes at 25° C. and 95% RH, the tress treated in accordance to the invention exhibited about 30% less water vapor sorption than the untreated control (FIG. 15). Without being bound by theory, it appears that the invention's formula and treatment created a film on the hair that resisted the naturally-occurring water weight gain. It is believed this mechanism may contribute to the anti-frizz benefits noted in earlier examples. Accordingly, other anhydride-containing polymers are contemplated for modulating the water sorptivity of hair, e.g., more hydrophobic or hydrophilic polymers. In one aspect, a more hydrophilic anhydride-containing polymer can be used to further minimize water pick-up and/or extend the anti-frizz effect. Alternatively, anhydride-containing polymers can be created that incorporate other benefits, such as shine agents, Example 307

The formulas of Examples 89, 91, and 94, each at pH 3, 7, and 11, were applied to a frizzy tress to determine their efficacy in providing a durable style. First, each tress was rinsed for 30 seconds in fresh, running water, then shampooed for 30 seconds using a non-care/non-conditioning shampoo, and then rinsed again in fresh, running water for 30 seconds. At this time the "untreated" tress (the control) was diffuse-dried in a dome hair dryer. Still-damp tresses to be tested in accordance with the invention received about 1 gram of the formula, which was worked into the hair fibers from tress clamp to tip. Excess formula was removed with the fingers. These treated tresses were flat-ironed at 205° C. using 4 passes at 5-6 seconds per pass, allowed to equilibrate for 30 minutes at room temperature and humidity. Then, to test the durability of the flat-iron style, each treated tress was rinsed, washed, rinsed, and dome dried as described in this Example. Tresses were not reused between conditions, as new tresses were used for each formula/pH.

Figure 16:
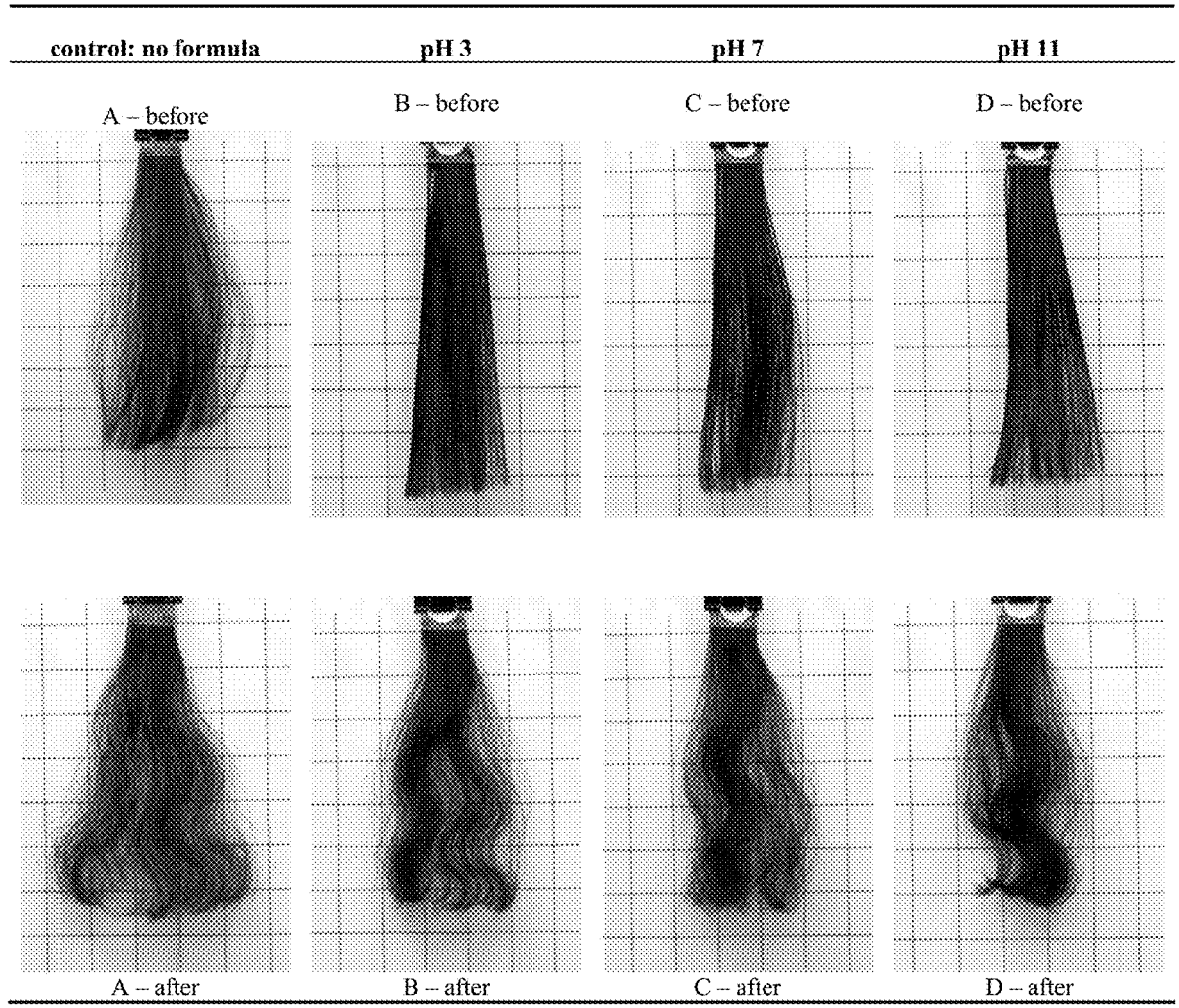
FIGS. 16 A-D, 17 A-D, and 18 A-D are before and after photographs of tresses produced in accordance with Example 307.
Figure 17:
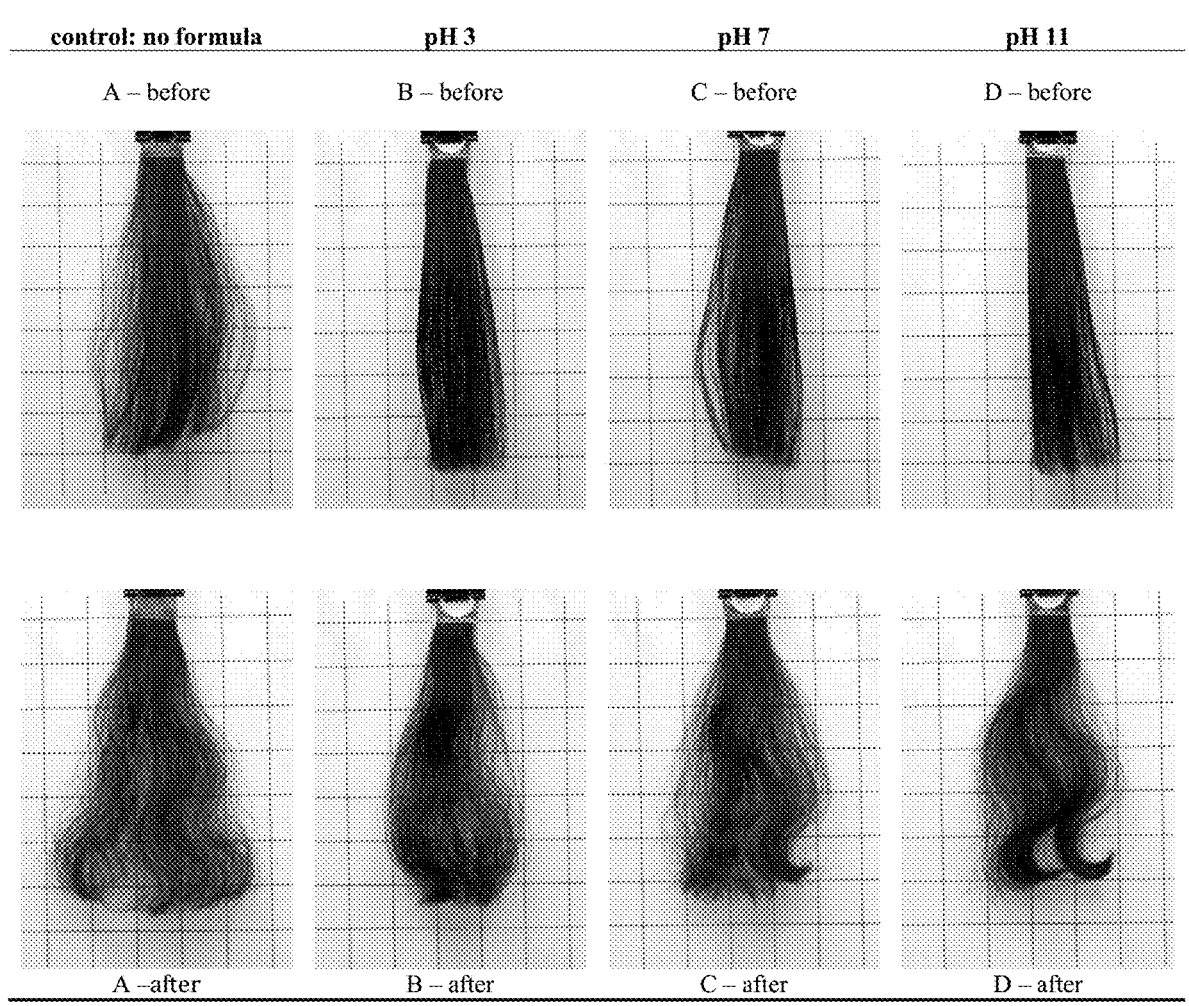
Figure 18:
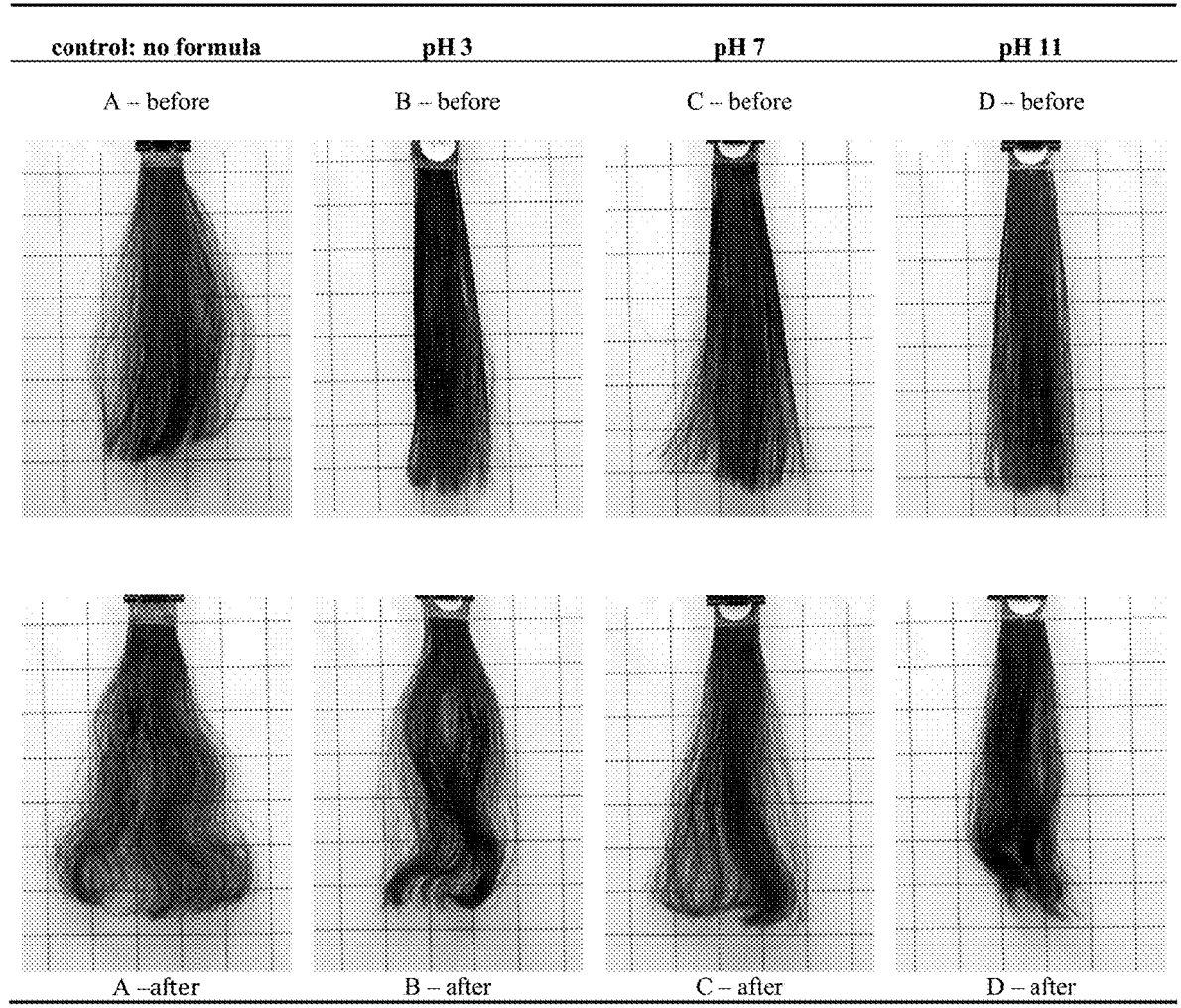

In each case, the formulas of the invention at the 3 pHs demonstrated a more durable style than the control that did not receive any formula (FIG. 16 A-D, 17 A-D, 18 A-D). Tresses treated with formulas having a pH of 7 and 11 exhibit less wave gain and better hair uniformity after styling and after washing than the tress treated with the pH 3 formula and the control tress.

Example 308

A composition of the invention was tested to determine its effect on preventing breakage due to thermal treatment. A single lock of hair was divided into two tresses, which were equally rinsed in fresh, running water, washed in a non-care/non-conditioning shampoo containing sodium laureth sulfate, and then rinsed again in fresh, running water. The tresses were dried with a hand-held dryer set on high until dry, and then combed. The control tress was flat ironed at 230° C. for 4 minutes, pulling the flat iron from the tress clamp to tip in about 12 seconds. The other still-damp tress was treated with 1.0 g of the Example 288 formula (diluted to 10% solids), which was worked from the tress clamp to hair tip. Excess formula was removed with the fingers before combing. Following this treatment, the tress was blow dried and flat ironed as previously described. After flat-ironing, the tresses were shampooed, rinsed, and blow dried. To assess breakage following the 4-minute flat ironing, each tress was combed from tress clamp-to-tip 100 times using a fine-toothed comb, and the broken hair pieces were collected from the entire surrounding area with tape and counted.

Figure 19:
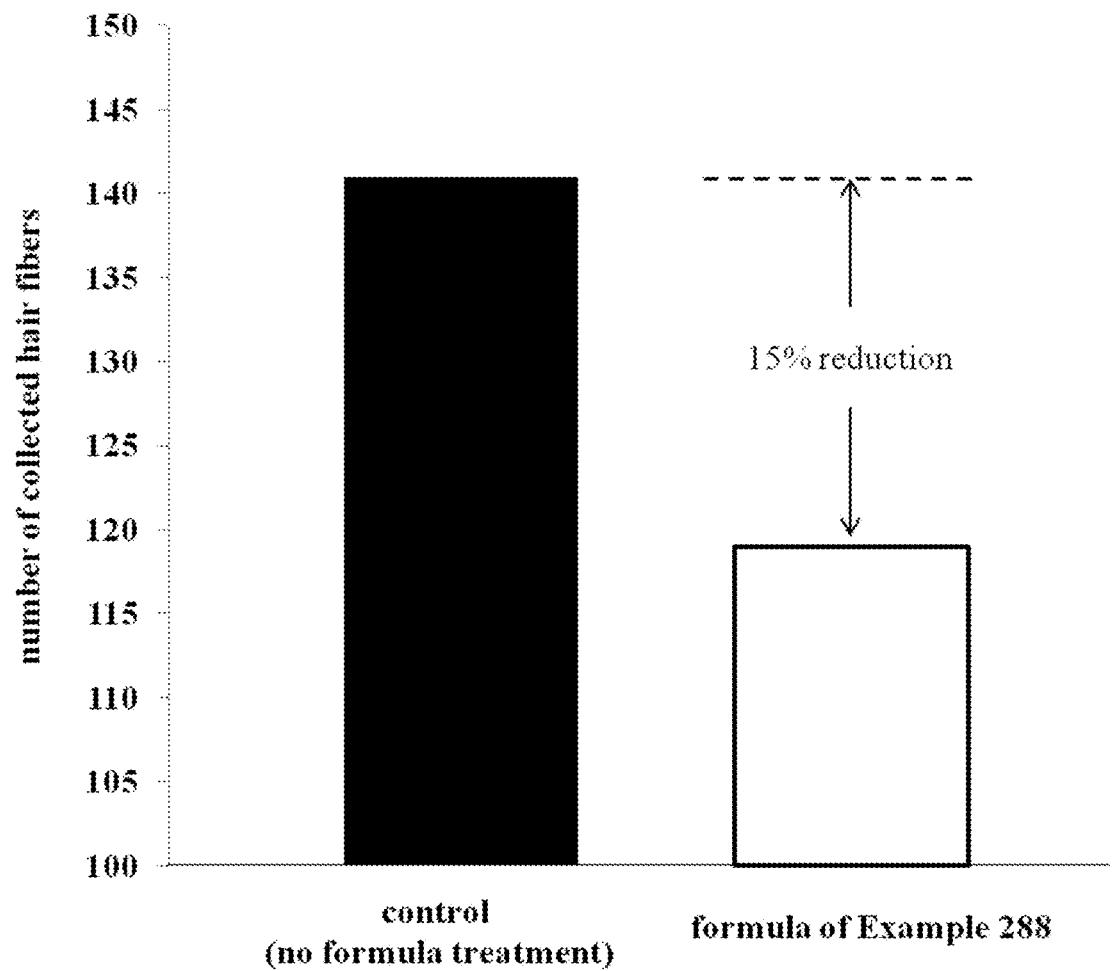
FIG. 19 is a graph of number of collected hair pieces as a function of treatment produced in accordance with Example 308.

The formula of Example 288 helped to protect hair from breakage after a thermal styling treatment, with about 15% fewer collected broken hair pieces compared to the control which did not receive any formula treatment (FIG. 19).

Example 309

The tresses of Example 308, flat ironed for 4 minutes at 230° C., were spectroscopically examined to determine tryptophan degradation. The method is described in a number of references, including the following publications, each of which is incorporated in its entirety by reference: U.S. Pat. No. 6,241,977; C. M. Pande and J. Jachowicz, "Hair photodamage-Measurement and prevention," *J. Soc. Cosmet. Chem.*, 44, 109-122, March/April 1993; J. Jachowicz, et al., "Photodegradation of hair and its photoprotection by a substantive photofilter," Drug & Cos. Ind., December 1995; B. Locke and J. Jachowicz, "Effect of formulation on the hair protection efficacy by a substantive photofilter," *Cos. and Toiletries Manuf. Worldwide*, (rest of reference). Briefly, the intensity of fluorescence emission is measured at 340-350 nm (excitation at 290 nm) for the control and formula-treated tresses. A reduction in the emission intensity is attributed to tryptophan thermal decomposition due to the flat iron.

Figure 20:
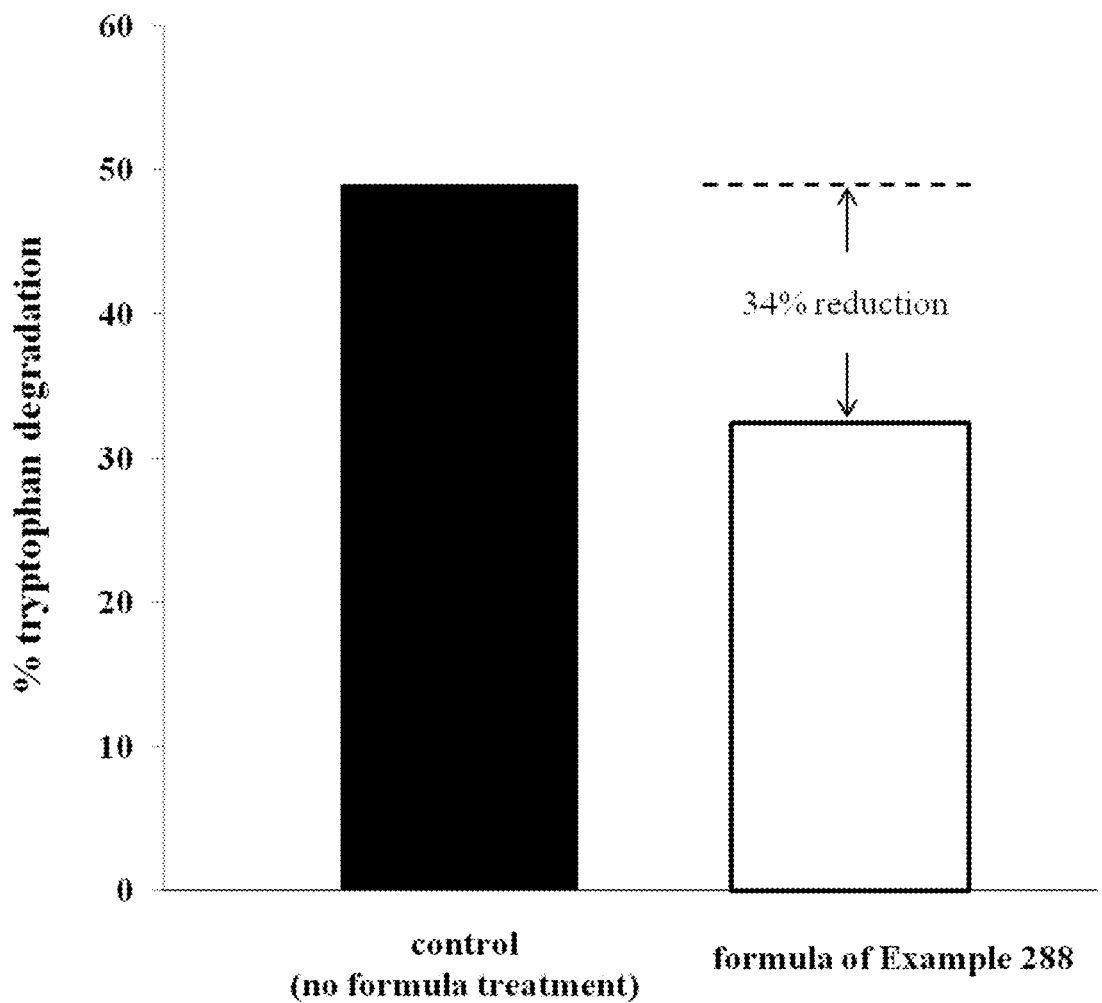
FIG. 20 is a graph of % tryptophan degradation as a function of treatment produced in accordance with Example 309.

The tress treated in accordance with the invention exhibited a 34% reduction in tryptophan degradation (FIG. 20), indicating the durable styling formula helped to protect the hair from the deleterious effects of heat during the flat ironing styling procedure. The consumer may perceive the reduced breakage (of Example 308) and/or tryptophan protection by a reduced combing/brushing force needed to style hair.

Examples 310-406

Durable styling control creams are formulated having the concentrated formulas of Examples 97-192 (Table 19). To make the control cream, water and hydroxyethylcellulose are placed in a container, dispersed, and heated to 75° C. Separately, the ingredients of phase B are combined with gentle heating and mixed until uniform. The pH is adjusted to 7.25±0.25 with 10% NaOH (as necessary). Phase B is added to phase B, and mixed until uniform. While this mixture cools to about 45° C.-50° C., phase C is prepared in a separate container by adding the ingredients individually, mixing until uniform after each addition. Once the A+B blend reaches the set temperature, phase C is added and mixed for 45 minutes. Phase D is added to the main batch, mixed well, and the control cream is removed from heat. Example 406 with Gantrez® S-97 was reduced to practice.

The product of Example 405 was an opaque, white cream and had a pH of about 7.6 and a Brookfield viscosity of 9,000±5,000 cP (using spindle RV7 at 10 rpm).

Table 19: The control cream formula of Example 309

| ingredient | trade name (supplier) | addition level (% w/w) |
|---|---|---|
| Phase A | | |
| deionized water | | 57.15 |
| hydroxyethylcellulose | Natrosol 250 HHR (Ashland) | 1.00 |
| Phase B | | |
| stearamidopropyl dimethylamine | Jeechem S-13 (Jeen) | 0.35 |
| behenyl alcohol and cetearyl alcohol and hydroxyethyl cetearamidopropyldimonium chloride | Prolipid ® 161 (ASI) | 1.00 |
| Phase C | | |
| durable styling formula of Example 97-192 | Styleze XT-3 (ASI) | 13.35 |
| deionized water | | 25.00 |
| glycerin and glyceryl acrylate/ acrylic acid copolymer | Lubrajel ® NP (ASI) | 0.50 |
| cyclopentasiloxane | Belsil CM040 (Wacker) | 0.50 |
| sodium polyacrylate | Rapthix ® A-100 (ASI) | 0.35 |
| Phase D | | |
| phenoxyethanol and caprylyl glycol | Optiphen ® (ASI) | 0.80 |
| total | | 100.00 |

Examples 407-503

Durable frizz control mousses are formulated having the concentrated formulas of Examples 97-192 (Table 20). To make the mousse, the water and PVM/MA decadiene copolymer are dispersed together in a contain while heating to 75° C. Following 45 minutes of mixing, the batch was cooled to about 35° C.-45° C. Meanwhile, in a second container the ingredients of Phase B are added individually, mixing until uniform after each addition. This material is added to Phase A with mixing. Meanwhile, in a third container the ingredient of Phase C are added individually, mixing until uniform after each addition. Then, this material is added to the mixed Phase A+B batch until uniform. The pH is adjusted to 7.25±0.25 with 50% NaOH solution. The formula is filled into vacuum crimp cans, and pressurized with the ingredients listed in Phase D. Example 503 with Gantrez® S-97 was reduced to practice.

The product of Example 503 was a mousse with a pH of 7.25±0.25 and a Brookfield viscosity of 900±300 cP (using spindle LV2 at 10 rpm).

TABLE 20

The control cream formula of Example 309

| ingredient | trade name (supplier) | addition level (% w/w) |
|---|---|---|
| Phase A | | |
| deionized water | | 35.50 |
| PVM/MA decadiene crosspolymer | Stabilize ® QM (ASI) | 0.50 |

TABLE 20-continued

The control cream formula of Example 309

| ingredient | trade name (supplier) | addition level (% w/w) |
|---|---|---|
| Phase B | | |
| deionized water | | 28.20 |
| glycerin and glyceryl acrylate/acrylic acid copolymer | Lubrajel ® NP (ASI) | 0.35 |
| durable styling formula of Example 97-192 | Styleze XT-3 (ASI) | 13.35 |
| phenoxyethanol (and) caprylyl glycol | Optiphen ® (ASI) | 0.60 |
| Phase C | | |
| deionized water | | 15.00 |
| PEG-PPG 25/25 dimethicone | Si-Tec ™ DMC 6031 (ASI) | 0.25 |
| cetrimonium chloride | Carsoquat ® CT-429 (Lonza) | 0.25 |
| Phase D | | |
| isobutane/propane | A-46 (Aeropres) | 2.00 |
| dimethyl ether | Dymel A (DuPont) | 4.00 |
| total | | 100.00 |

Examples 504

Two durable styling compositions according to the invention are prepared having the ingredients shown in Table 21. Formula #2 contains the same ingredients as #1, but also contains hydrogen peroxide. This study's tresses are prepared by first rinsing them for 30 seconds in clear, running water, washing them for 30 seconds using a non-care/non-conditioning shampoo, and then rinsing again for 30 seconds in clear, running water. About 1 g of each formula is applied to still-damp frizzy tresses (excess formula is removed from the tresses with the fingers), which are then blow dried straight. Treated tresses are flat-ironed at 205° C. using 4 passes at 5-6 seconds per pass, allowed to equilibrate for 30 minutes at room temperature and humidity. Then, to test the durability of the flat-iron style to repeated wash cycles, each treated tress is rinsed, washed, rinsed, and dome dried as described in this Example.

Both tresses maintain the initial flat-iron style after washing, evidenced by a reduction in the tress width. The tress treated with formula #2 better retains the durable style after multiple washing compared to the tress treated with formula #1.

TABLE 21

The peroxide-initiated durable styling compositions of Example 504

| | | addition level (% w/w) | |
|---|---|---|---|
| ingredient | trade name (supplier) | #1 | #2 |
| deionized water | | 87.0 | 77.0 |
| PVM/MA copolymer | Gantrez ® S-97 (ASI) | 2.0 | 2.0 |
| NaOH solution | | pH to 10 | pH to 10 |
| VP/DMAPA acrylates copolymer | Styleze ® CC-10 (ASI) | 10.0 | 10.0 |
| phenoxyethanol (and) caprylyl glycol | Optiphen ® (ASI) | 1.0 | 1.0 |
| hydrogen peroxide (35% solution) | | | 10.0 |
| total | | 100.0 | 100.0 |

The invention claimed is:

1. A method of providing a durable hair style comprising the steps:
    applying to the hair a composition consisting of:
        a poly(vinyl methyl ether-co-maleic anhydride), and
        a polyimide-1; and
        a blend of caprylyl glycol and phenoxyethanol; and
        heating the hair to a temperature ranging from about 90° C. to about 250° C., wherein the composition is left in the hair to exhibit at least one of greater shine, conditioning, defrizzing, decurling, dewaving, curling, waving, softness, ease of styling, volume improvement, smooth feeling, improved hair alignment, manageability, color protection, or humidity resistance.

2. The method of claim 1, wherein the composition has a pH of from 3 to 11.

3. The method of claim 2, wherein the composition has a pH of from 3 to 7.

4. The method of claim 2, wherein the composition has a pH of from 7 to 11.

5. The method of claim 1, wherein the composition has a pH of 12.

6. The method of claim 1, wherein the composition has a pH of 13.

7. The method of claim 1, wherein the composition further comprises about 93.92% to about 98.17% water.

8. The method of claim 1, wherein the composition further comprises a solvent comprising water and a lower molecular weight alcohol.

9. A method of providing a durable hair style comprising the steps:
    applying to the hair a composition consisting of:
        a poly(vinyl methyl ether-co-maleic anhydride) copolymer selected from the group consisting of a poly(vinyl methyl ether-co-maleic anhydride), an ethyl ester of a poly(vinyl methyl ether-co-maleic anhydride), a butyl ester of a poly(vinyl methyl ether-co-maleic anhydride), an isopropyl ester of a poly(vinyl methyl ether-co-maleic anhydride), and combinations thereof,
        a polyimide-1,
        water,
        sodium hydroxide, and
        a blend of caprylyl glycol and phenoxyethanol; and
        heating the hair at a temperature ranging from about 90° C. to about 250° C.

10. The method of claim 9, wherein the poly(vinyl methyl ether-co-maleic anhydride) copolymer is a poly(vinyl methyl ether-co-maleic anhydride).

11. The method of claim 9, wherein the poly(vinyl methyl ether-co-maleic anhydride) copolymer is an ethyl ester of a poly(vinyl methyl ether-co-maleic anhydride).

12. The method of claim 9, wherein the poly(vinyl methyl ether-co-maleic anhydride) copolymer is of a butyl ester of a poly(vinyl methyl ether-co-maleic anhydride).

13. The method of claim 9, wherein the poly(vinyl methyl ether-co-maleic anhydride) copolymer is of an isopropyl ester of a poly(vinyl methyl ether-co-maleic anhydride).

14. A method of providing a durable hair style comprising the steps:
applying to the hair a composition consisting of:
a poly(vinyl methyl ether-co-maleic anhydride) copolymer selected from the group consisting of a poly(vinyl methyl ether-co-maleic anhydride), an ethyl ester of a poly(vinyl methyl ether-co-maleic anhydride), a butyl ester of a poly(vinyl methyl ether-co-maleic anhydride), an isopropyl ester of a poly(vinyl methyl ether-co-maleic anhydride), combinations thereof, and
a polyimide-1; and
a blend of caprylyl glycol and phenoxyethanol; and
heating the hair at a temperature ranging from about 90° C. to about 250° C.

15. The method of claim 14, wherein the poly(vinyl methyl ether-co-maleic anhydride) copolymer is an ethyl ester of a poly(vinyl methyl ether-co-maleic anhydride).

16. The method of claim 14, wherein the poly(vinyl methyl ether-co-maleic anhydride) copolymer is a butyl ester of a poly(vinyl methyl ether-co-maleic anhydride).

17. The method of claim 14, wherein the poly(vinyl methyl ether-co-maleic anhydride) copolymer is an isopropyl ester of a poly(vinyl methyl ether-co-maleic anhydride).

* * * * *